United States Patent
He et al.

(10) Patent No.: US 11,672,511 B2
(45) Date of Patent: Jun. 13, 2023

(54) HIGH RESOLUTION INTRAVASCULAR ULTRASOUND IMAGING SYSTEMS AND METHODS

(71) Applicant: InfraReDx, Inc., Burlington, MA (US)

(72) Inventors: Zhihua He, Reading, MA (US); David Erickson, Topsfield, MA (US); Glen McLaughlin, San Carlos, CA (US)

(73) Assignee: InfraReDx, Inc., Burlington, MA (US)

( * ) Notice: Subject to any disclaimer, the term of this patent is extended or adjusted under 35 U.S.C. 154(b) by 1038 days.

(21) Appl. No.: 16/182,340

(22) Filed: Nov. 6, 2018

(65) Prior Publication Data

US 2019/0069883 A1 Mar. 7, 2019

Related U.S. Application Data

(63) Continuation of application No. 13/967,905, filed on Aug. 15, 2013, now Pat. No. 10,245,007.

(Continued)

(51) Int. Cl.
*A61B 8/08* (2006.01)
*A61B 8/12* (2006.01)
(Continued)

(52) U.S. Cl.
CPC ............ *A61B 8/5207* (2013.01); *A61B 8/085* (2013.01); *A61B 8/0891* (2013.01); *A61B 8/12* (2013.01);
(Continued)

(58) Field of Classification Search
CPC ..... A61B 8/5207; A61B 8/085; A61B 8/0891; A61B 8/12; A61B 8/445; A61B 8/4461;
(Continued)

(56) References Cited

U.S. PATENT DOCUMENTS 3,697,955 A * 10/1972 Bryden ................... G09G 1/18
345/27
4,561,019 A 12/1985 Lizzi et al.
(Continued)

FOREIGN PATENT DOCUMENTS

EP 1214910 B1 6/2002
EP 1 750 144 A1 2/2007
(Continued)

OTHER PUBLICATIONS

Bayer, "Anti-aliasing filter", 2020 (Year: 2020).*
(Continued)

*Primary Examiner* — Katherine L Fernandez
*Assistant Examiner* — Brooke Lyn Klein
(74) *Attorney, Agent, or Firm* — Rothwell, Figg, Ernst & Manbeck, P.C.

(57) ABSTRACT

Disclosed is a high resolution intravascular ultrasound imaging system including a catheter with a rotatable imaging assembly and an image processor. The image processor in turn features a pulser configured to energize the ultrasound transducer of the rotatable imaging assembly with a multi-frequency ultrasound waveform signal. The image processor further contains a receiver configured to decompose received ultrasound energy as reflected by the target vessel into a plurality of individual subband signals, individually process these signals and reconstitute these signals into a high resolution image of the blood vessel. The IVUS system of the invention may be useful in characterizing cap thickness of vulnerable plaques or other detailed studies of blood vessels.

13 Claims, 19 Drawing Sheets

Related U.S. Application Data

(60) Provisional application No. 61/794,868, filed on Mar. 15, 2013.

(51) Int. Cl.
   *A61B 8/00* (2006.01)
   *G01S 7/52* (2006.01)
   *G01S 15/89* (2006.01)

(52) U.S. Cl.
   CPC ............ *A61B 8/445* (2013.01); *A61B 8/4461* (2013.01); *A61B 8/4483* (2013.01); *A61B 8/5269* (2013.01); *G01S 7/5202* (2013.01); *G01S 7/52036* (2013.01); *G01S 7/52077* (2013.01); *G01S 15/8952* (2013.01); *G01S 15/8959* (2013.01)

(58) Field of Classification Search
   CPC ... A61B 8/4483; A61B 8/5269; G01S 7/5202; G01S 7/52036; G01S 7/52077; G01S 15/8952; G01S 15/8959
   See application file for complete search history.

(56) References Cited

U.S. PATENT DOCUMENTS

| | | | | |
|---|---|---|---|---|
| 4,799,177 | A * | 1/1989 | Sarr | G01B 7/02 702/171 |
| 5,549,111 | A * | 8/1996 | Wright | G01S 15/895 600/443 |
| 5,891,038 | A | 4/1999 | Seyed-Bolorforosh et al. | |
| 6,048,312 | A * | 4/2000 | Ishrak | A61B 8/0833 128/916 |
| 6,095,977 | A | 8/2000 | Hall et al. | |
| 6,213,947 | B1 | 4/2001 | Phillips | |
| 6,385,329 | B1 | 5/2002 | Sharma | |
| 6,469,646 | B1 * | 10/2002 | Song | H03M 1/687 341/145 |
| 8,532,360 | B2 | 9/2013 | Suri | |
| 2002/0175835 | A1 * | 11/2002 | Falik | H03M 11/20 341/26 |
| 2004/0158147 | A1 * | 8/2004 | Shifrin | G01S 7/5202 600/437 |
| 2004/0236222 | A1 | 11/2004 | Mao et al. | |
| 2006/0184023 | A1 * | 8/2006 | Satoh | G01S 7/52047 600/437 |
| 2006/0253031 | A1 * | 11/2006 | Altmann | A61B 8/483 600/466 |
| 2008/0264171 | A1 | 10/2008 | Wodnicki | |
| 2009/0209858 | A1 | 8/2009 | Oelze | |
| 2009/0281430 | A1 | 11/2009 | Wilder | |
| 2010/0305442 | A1 | 12/2010 | Tierney et al. | |
| 2011/0087104 | A1 | 4/2011 | Moore et al. | |
| 2011/0184289 | A1 | 7/2011 | Oshiki et al. | |
| 2011/0231160 | A1 | 9/2011 | Suzuki | |
| 2012/0078099 | A1 | 3/2012 | Sun | |
| 2015/0119716 | A1 | 4/2015 | Shen | |

FOREIGN PATENT DOCUMENTS

| | | |
|---|---|---|
| JP | 09000522 A | 1/1997 |
| JP | 2005342141 A | 12/2005 |
| JP | 2006-217942 A | 8/2006 |
| JP | 2007-185525 A | 7/2007 |
| JP | 2008-272471 A | 11/2008 |
| JP | 2011193914 A | 10/2011 |
| JP | 2013507227 A | 3/2013 |
| WO | 9501751 A1 | 1/1995 |
| WO | 2009/148068 A1 | 12/2009 |
| WO | 2009146414 A1 | 12/2009 |
| WO | 2011046903 A2 | 4/2011 |

OTHER PUBLICATIONS

Rao, Navalund, et al., "Multispectral ultrasound imaging and analysis of speckle generating medium," RIT Scholar Works, Rochester Institute of Technology, 1993.

Office Action Summary (English language) regarding Japanese Patent Apliction No. 2016500179, 2 pages (Aug. 3, 2017).

Office Action (Japanese language) issued in Japanese Patent Application No. 2016500179, 7 pages (Aug. 3, 2017).

Written Opinion and Search Report of the International Searching Authority for PCT/US2014/013178, dated Apr. 25, 2014, 13 pages.

Official Communication issued in European Application No. 14 706 710.2 on Jan. 4, 2019, 4 pages.

Extended European Search Report issued in European Application No. 18 17 7168.4 dated Jan. 22, 2019, 5 pages.

Office Action issued in Japanese Application No. 2018-097721 dated Apr. 2, 2019, including English Office Action Summary, 6 pages.

\* cited by examiner

HIGH RESOLUTION INTRAVASCULAR ULTRASOUND IMAGING SYSTEMS AND METHODS

CROSS-REFERENCE DATA

The present application is a continuation of U.S. patent application Ser. No. 13/967,905, filed on Aug. 15, 2013, which claims the benefit of priority to U.S. Provisional Patent Application No. 61/794,868 filed Mar. 15, 2013, each of which are incorporated herein by reference in their entireties.

BACKGROUND

The present invention relates generally to intravascular ultrasound imaging (IVUS). More particularly, the invention describes a novel IVUS system with high contrast resolution and high spatial resolution using pulse compression and frequency compounding.

IVUS imaging is generally performed for assessment of coronary artery disease and to guide percutaneous coronary interventions, typically the placement of a stent.

Atherosclerotic lesions that are prone to rupture, so called vulnerable plaques, are of increasing interest to interventional cardiologists. One type of vulnerable plaque thought to be responsible for a large percentage of plaque ruptures is a thin-cap fibroatheroma wherein a thin (<65 µm) fibrous cap overlies a mechanically unstable lipid-rich or necrotic core. Current commercially available IVUS systems operate up to only 40 MHz and have axial resolutions that are limited to approximately 100 µm. Consequently, current commercially available IVUS systems cannot measure the cap thickness of vulnerable plaques.

Resolution of current commercial IVUS is inadequate to characterize neointima, the thin layer of tissue that forms over a stent as the vessel heals post-deployment. Stent struts could be better visualized and their apposition assessed with higher resolution imaging. Other features of pathological interest such as thrombus, small dissections, and small calcifications can be better visualized with higher resolutions imaging.

It is generally necessary to increase the transducer frequency in order to improve spatial resolution of the IVUS system. However, increased imaging frequency also leads to reduced contrast between blood and non-blood tissue that in turn makes segmentation of the blood-filled lumen from the intimal plaque difficult. Increasing transducer frequency may also suffer from higher tissue attenuation leading to lower Signal-to-Noise Ratio and resulting in lower contrast resolution. Some automatic segmentation algorithms exploit the frequency-dependent ultrasound properties of blood and non-blood tissues as described for example in U.S. Pat. No. 5,876,343 by Teo. Real-time, automatic segmentation tools are often prone to errors, which reduce their utility in clinical practice.

Some prior art examples of multi-frequency imaging systems are disclosed in U.S. Pat. Nos. 5,876,343 and 6,139,501 and U.S. Patent Application Publication No. 2011/0087104, which are incorporated herein by reference in their respective entireties.

Multi-frequency IVUS imaging can also be generally achieved by use of multiple transducer imaging catheters. However, multiple transducers add complexity and cost to the disposable imaging catheter and the imaging system. The potential need to co-register the images from the separate transducers further complicates their practical use.

There exists a need for a technology that provides higher contrast resolution for improved assessment of coronary arteries while still providing sufficient spatial resolution to characterize stent healing and vulnerable plaques. Further, it is desirable that such a technology does not require any co-registration step between multiple images. Still further, it is desirable that such a technology does not substantially increase system and catheter complexity and cost over existing commercial systems and catheters.

SUMMARY

It is an object of the present invention to overcome these and other drawbacks of the prior art by providing a novel high resolution IVUS system and methods for ultrasound imaging using the concepts of pulse compression and frequency compounding.

It is another object of the present invention to provide a novel coded pulser suitable for operating the small size, single-transducer IVUS catheter supporting the imaging methods described herein.

The present invention provides a novel high resolution intravascular ultrasound imaging system comprising: a catheter and an image processor. The catheter of the system may be configured for percutaneous insertion and includes an elongated body containing a rotatable imaging assembly. The imaging assembly in turn includes an ultrasound transducer located near the distal end of the catheter, which may be energized by one or more electrical conduits. The ultrasound transducer may be configured to emit ultrasound energy towards the target blood vessel while rotating about the longitudinal axis of the catheter. The ultrasound transducer may be further configured to receive the ultrasound energy reflected by the target vessel and transmit the received signal to the image processor.

The image processor may include a pulser and a receiver. The pulser may be configured to energize the ultrasound transducer through the electrical conduits with a multi-frequency waveform signal. The receiver may be configured to receive and decompose the reflected ultrasound energy into a plurality of individual subband signals, individually process this plurality of subband signals, and then reconstitute the plurality of subband signals into one or more imaging signals representing the target blood vessel.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 1c shows an expanded example of frequency compounding operations of FIG. 1a;

DETAILED DESCRIPTION OF PREFERRED EMBODIMENTS

Figure 1A:
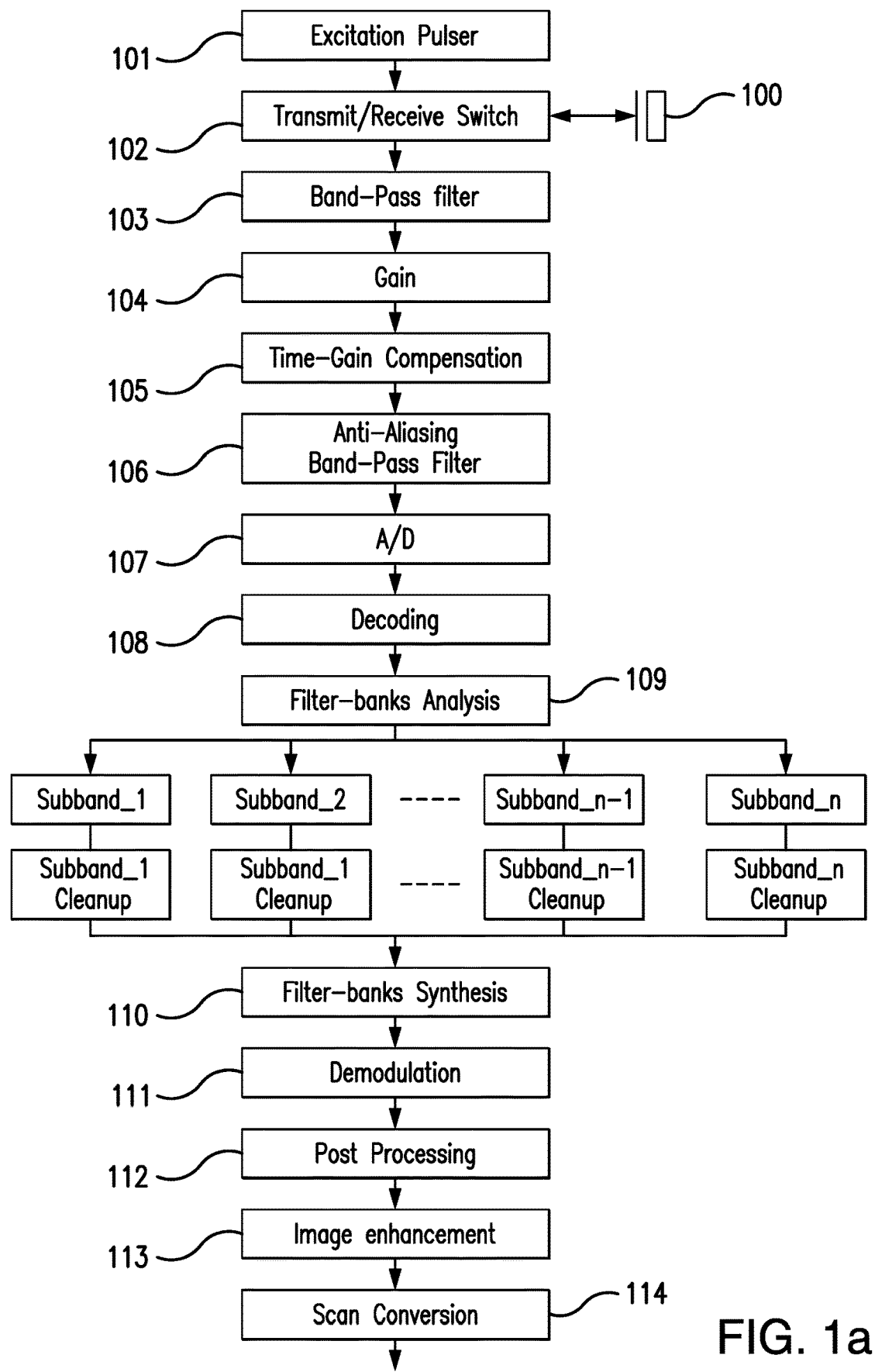
FIG. 1a is a first method flowchart for IVUS signal generation and processing aimed to achieve high contrast and high spatial resolution at the same time.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

In general, the IVUS catheter and imaging system of the invention may include a catheter having an elongated body with a distal end configured for percutaneous introduction into a vascular system of a patient. The catheter may further include an imaging assembly configured to be inserted into or contained in the elongated body of the catheter. The imaging assembly may include one of more electrical conduits connected to a piezoelectric transducer located generally at or close to the distal end of the catheter. The electrical conduits and the piezoelectric transducer may be configured to emit ultrasonic energy away from the distal end of the catheter and directed at the target tissue. The imaging assembly may be further configured to receive reflected ultrasonic energy. The imaging assembly may be configured to rotate about the longitudinal axis of the catheter so as to emit and receive ultrasonic energy circumferentially in all radial directions around the catheter.

The system of the invention may further include an image processor comprising a pulser and a receiver, the image processor is operably coupled to the imaging assembly and arranged for the pulser to provide the imaging assembly with a coded multi-frequency or broadband waveform signal to cause the piezoelectric transducer to emit the ultrasonic energy towards the target tissue. The image processor may be further configured for the receiver to receive the reflected echo signal from the piezoelectric transducer and to generate a received waveform signal. The image processor may be further configured to decode the received waveform signal, followed by decomposition into a plurality of individual subband signals including a full bandwidth signal, individually process each subband signal and then reconstitute the subband signals into one or more imaging signals representing the target intravascular tissue such as a coronary artery or a structure such as a stent.

Novel Frequency Compounding and Pulsing Strategies, Systems and Methods

FIG. 1a shows a first method flowchart for IVUS signal generation and processing aimed to achieve high contrast and high spatial resolution at the same time. The piezoelectric transducer 100 may be excited by the selected excitation pulser 101 through a transmit/receive (T/R) switch 102 so as to cause the piezoelectric transducer 100 to emit ultrasound energy towards the target tissue. The transducer 100 may be a piezoelectric ceramic/polymer composite transducer, a piezoelectric single crystal Pb(Mg1/3Nb2/3)O3-PbTiO3 (PMN-PT) and Pb(In1/3Nb2/3)O3-Pb(Mg1/3Nb2/3)O3-Pb-TiO3 (PIN-PMN-PT) composite transducer. The transducer 100 may have one or multiple matching layers. The transducer 100 may be shaped to be round, square or another appropriate shape.

The returned echo signal received by the transducer 100 may then be transmitted through T/R switch 102 to a bandpass filter 103. Here the excitation pulser 101 may be a regular pulser or a coded pulser, for example a chirp pulser as described below. The received signal may then be boosted through a low-noise gain amplifier 104, followed by time-gain compensation (TGC) 105 to reduce the impact of depth-dependent tissue attenuation. The signal may then be passed through an anti-aliasing band-pass filter 106 before proceeding to the analog-to-digital A/D converter 107.

The digitized radio frequency (RF) signal represents the received echo signal and may then be passed through a decoding block 108, which corresponds to the selected excitation pulser 101. The decoded signal may then be passed through a filter-bank analysis operation 109: multiple subband data may be generated. The filter-bank analysis may be a family of widely used tools to decompose the signal into multiple components (subbands) with different frequency characteristics. One exemplary group of filter-bank analysis may be a discrete wavelet decomposition. For each subband data, the corresponding cleanup block may be designed to boost the feature of interest, e.g. tissue texture, and suppress artifacts, e.g. noisy speckles like blood speckle. After cleanup operations, the processed subband data may be passed through filter-bank synthesis block 110, which yields a single channel RF signal. Corresponding to filter-bank analysis block 109, the filter-bank synthesis block 110 combines the subband data for reconstruction. An example of such reconstruction may be a discrete wavelet reconstruction. In some embodiments, the filter bank may be a linear operation of combining subband data. In other embodiments, the filter bank operation of combining subband data may be non-linear: subband data sets may be combined in an adaptive manner (i.e., based on the differences of their values, ratio of their values, etc.).

For the purposes of this description, the operations between filter-bank analysis 109 and filter-bank synthesis 110 are together referred to as frequency compounding.

After filter-bank synthesis 110, the RF signal may be demodulated through demodulation block 111 for envelope detection, which may include standard mixer, low-pass filter, down-sampling, and amplitude operations. The envelope signal may then be passed through certain standard post-processing 112, e.g. digital Time Gain Compensation (TGC) and log compression. Before converting the envelope signal (which may be collected in polar domain) to Cartesian domain through scan conversion 114, the data may be passed through standard image enhancement block 113 to further boost the visualization of IVUS image through contrast control and de-speckle operations.

Figure 1B:
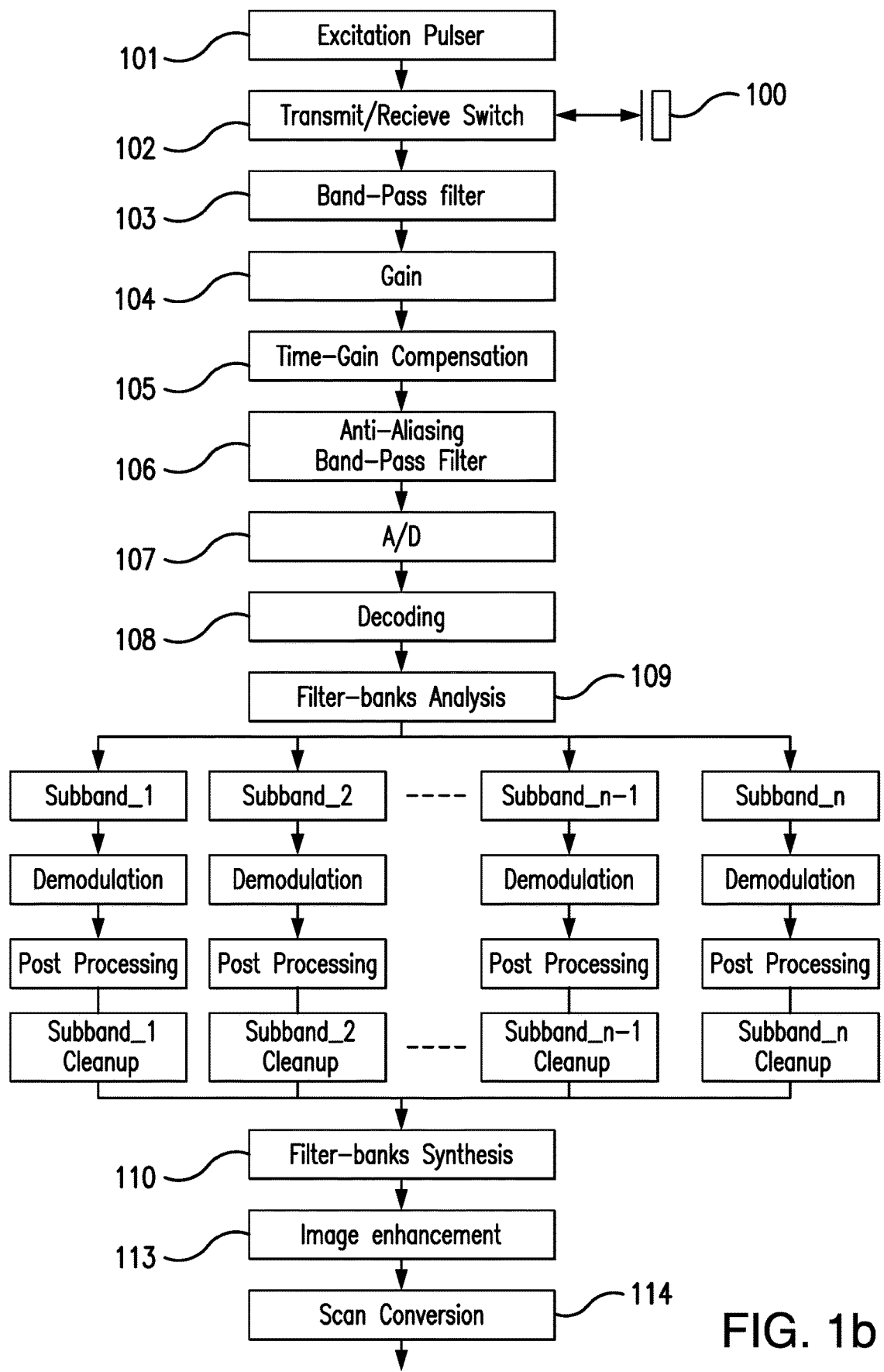
FIG. 1b is a second method flowchart for IVUS signal generation and processing.

FIG. 1b shows a second exemplary method flowchart for IVUS signal pipeline. As compared to FIG. 1a, same operations may be performed before filter-bank analysis 109. After different subband data is generated though, each subband data may be passed through a respective demodulation block and post-processing block before entering its corresponding cleanup block. The resulted processed subband data may then be combined through filter-bank synthesis block 110 before passing into image enhancement block 113 and scan conversion block 114.

Figure 1C:
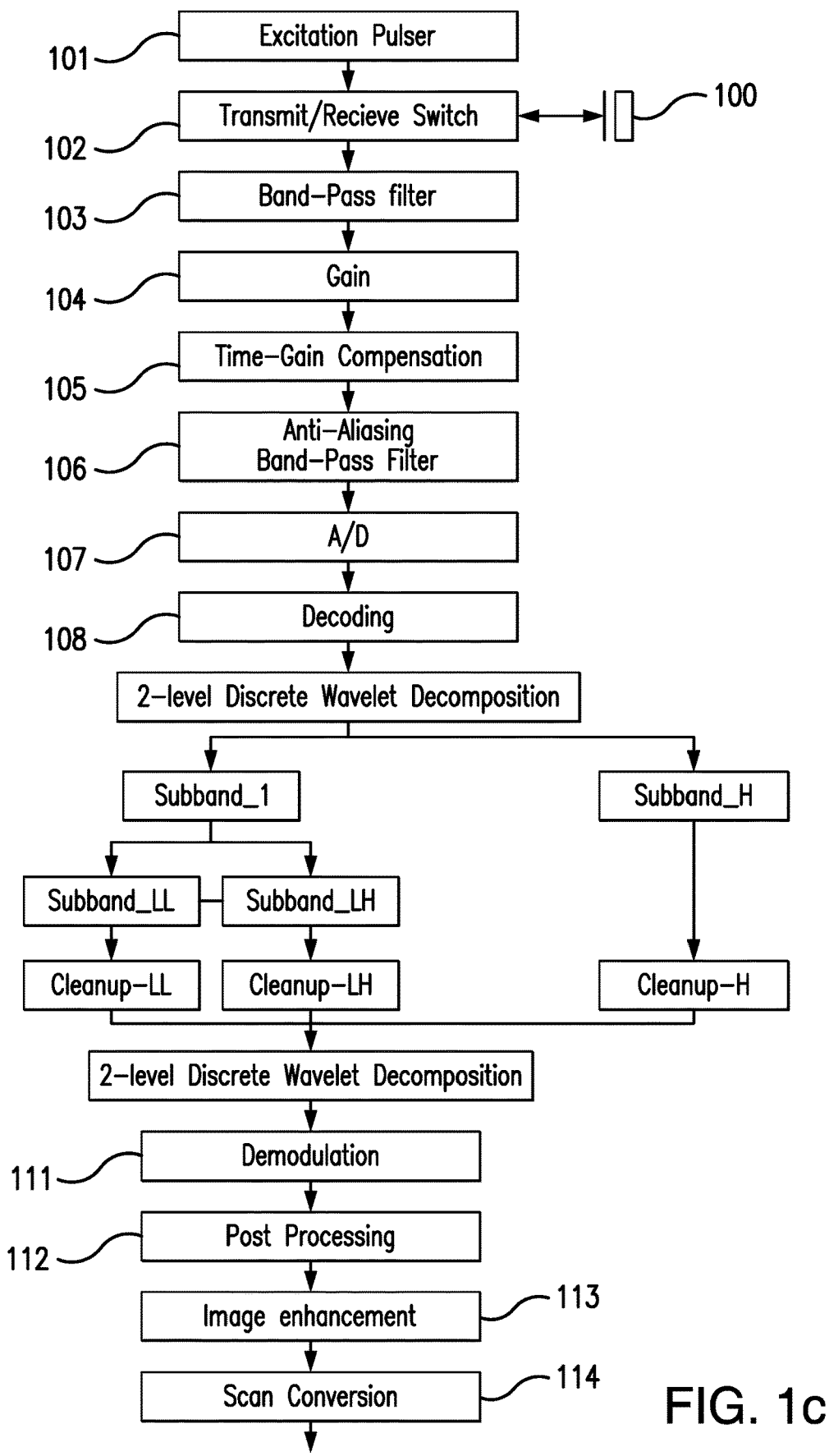

FIG. 1c shows an expanded example of frequency compounding operations of FIG. 1a. The RF signal after decoding may be passed through a two-level discrete wavelet decomposition, the wavelet may be as simple as a Haar wavelet or a more complex general Daubechies wavelet, or another wavelet. The two-level wavelet decomposition may be used to first generate subband_H at higher frequency and subband_L at lower frequency on the first level, then subband_L may be further decomposed into respective subband_LL and subband_LH on the second level. Following such decomposition, subband_H contains high-frequency components at a fine scale, subband_LL contains low-frequency components at a coarser scale and subband_LH contains high-frequency components at a coarser scale. For each subband, the corresponding cleanup operation may be independently performed. For example, for subband_H, denoise operation, which preserves coefficients greater than a predetermined threshold, may be adopted to suppress the speckle noise. For subband_LH, denoise operation, which uses linear/non-linear filter, may be adopted to further suppress the speckle noise of coarser scale. For subband_LL, a depth-dependent gain/gamma correction may be adopted to boost the depth penetration. After cleanup operation, the processed RF signal may be reconstructed through 2-level discrete wavelet reconstruction, followed by other steps shown in FIG. 1a.

In embodiments, different frequency-subband signals and individual subband processing may be used to perform speckle suppression and feature extraction. For example, low-frequency subband has good blood speckle suppression, which may be used directly to derive a mask for blood speckle suppression. The term "mask" is used here to describe a map, such as a binary map—for example a two-dimensional matrix with only zeros (0s) and ones (1s), in which ones are referring to regions of blood speckle, and zeros are referring to non-blood speckle region. This mask may be used as an overlay to help the user better identify key features like the vessel lumen. The mask may also be processed independently to improve or enhance continuity at the boundaries. In other embodiments, low-frequency subband and high-frequency subband may be combined together to derive a mask for general speckle suppression. Blood speckle may be an important feature identified in the near field.

In other embodiments, multiple subband signals may be used to derive a mask based on the different frequency response of the tissue signal for feature detection and corresponding feature enhancement. In yet further embodiments, the generated mask may be combined with the full-bandwidth signal, using either additive or multiplication operations.

Figure 1D:
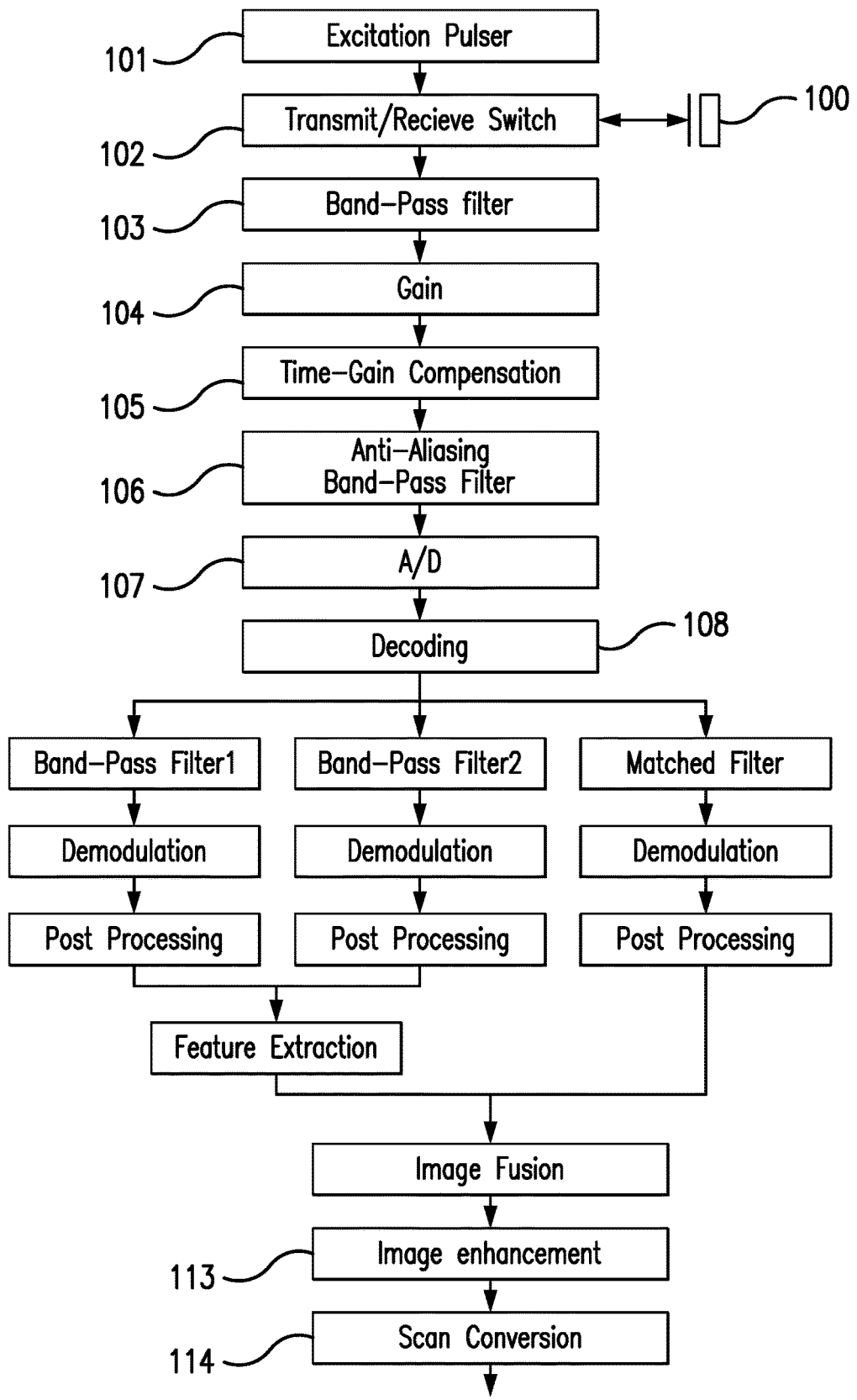
FIG. 1d shows an example of a system configured to achieve frequency compounding operations of FIG. 1b.

FIG. 1d shows one implementation example to achieve frequency compounding operations of FIG. 1b. The RF signal after decoding may be passed in parallel through three different band-pass filters: band-pass filter 1 with center frequency lower than transducer's native center frequency; band-pass filter 2 with center frequency greater than transducer's native center frequency; and matched filter, which covers the full bandwidth of the transducer. For example, for a piezoelectric transducer with native center frequency of 50 MHz and 100% bandwidth, filter 1 may be selected with a pass-band range of 25 MHz to 45 MHz, filter 2 may be selected with a pass-band range of 55 MHz to 75 MHz, and the match filter may be selected with a pass-band range of 25 MHz to 75 MHz.

The corresponding subband data therefore may provide low-frequency, high-frequency and full-bandwidth information. Each channel may then be passed through demodulation and post processing blocks such as those shown in FIG. 1b. The subband cleanup operations shown in blocks in FIG. 1b are summarized in a feature extraction block in FIG. 1d. The feature of interest (like blood speckle and tissue in far field) may be captured in both low-frequency and high-frequency subband; therefore feature extraction block may only use the information from those two subbands, for example the linear combination of low-frequency subband (with positive weight) and high-frequency subband (with negative weight). The full-bandwidth subband preserves full-spatial resolution—it may be combined with features maps from feature extraction through an image fusion block. The image fusion block, which can include additive, multiplicative, convolution or other operations, corresponds to filter-bank synthesis shown in FIG. 1b.

In embodiments, the subband designation may be adjusted or selected by the user so as to enable the user to specify and change the feature of interest.

In further embodiments, data averaging/summation (coherently) may be done after synthesis 110 with different frequency pulses resulting in a broader band signal for improved detail and contrast resolution.

Figure 1E:
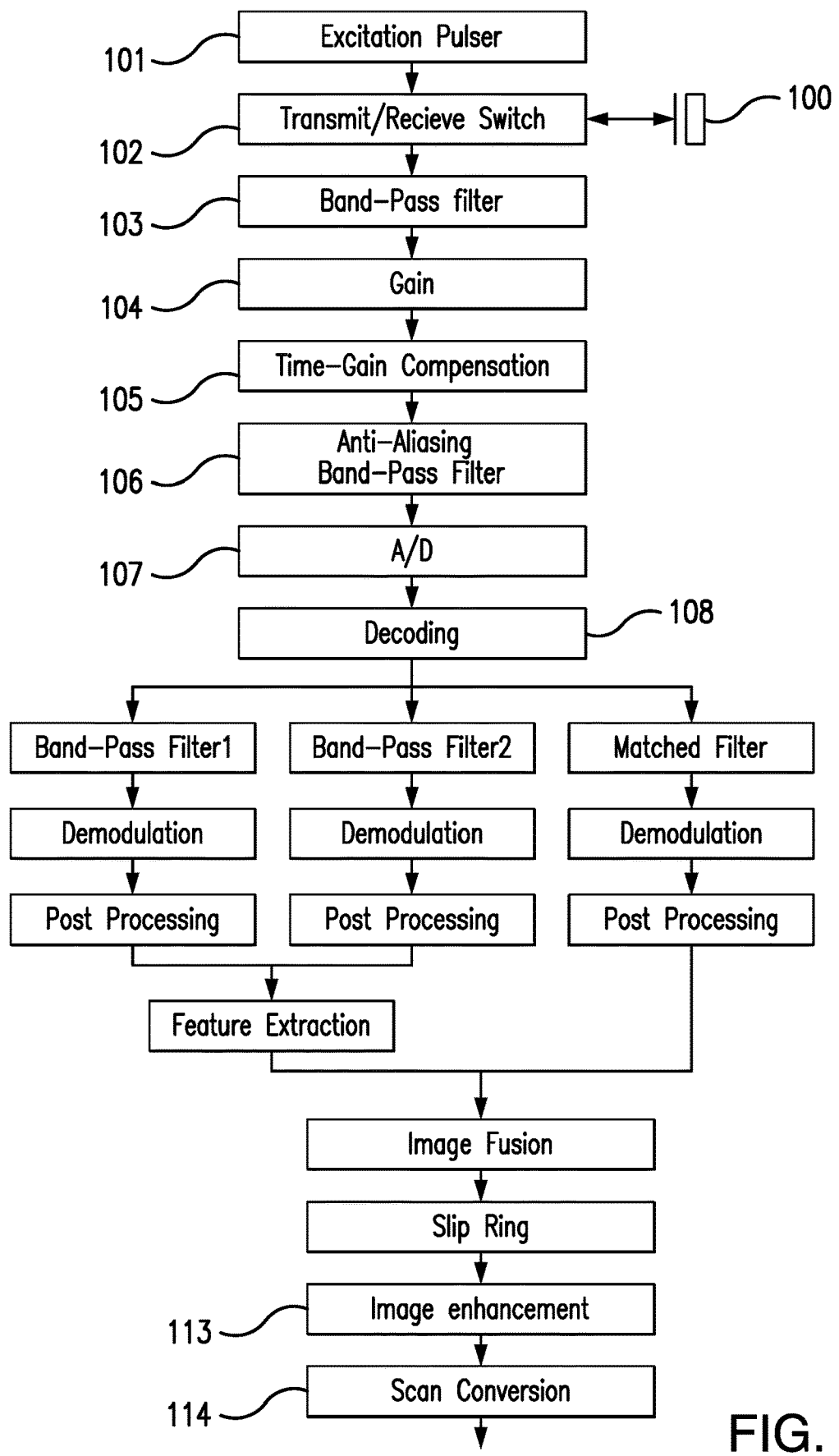
FIG. 1e shows an implementation example aimed at achieving frequency compounding operations of FIG. 1d.

FIG. 1e shows one exemplary implementation of frequency compounding methods shown in FIG. 1d. This figure illustrates where different operations take place physically.

All operations 100-106 before A/D block 107 may be performed in the analog domain using analog circuits. All operations between A/D 107 and the slip ring may be implemented on either a field-programmable gate array (FPGA) or a digital signal processing (DSP) chip, which may rotate with the IVUS catheter. The remaining operations after the slip ring may be implemented in stationary printed circuit board, e.g. FPGA, DSP, graphical processing unit (GPU), central processing unit (CPU), . . . etc. This arrangement may also be applied to method operations shown in FIGS. 1*a* through 1*c*.

Figure 1F:
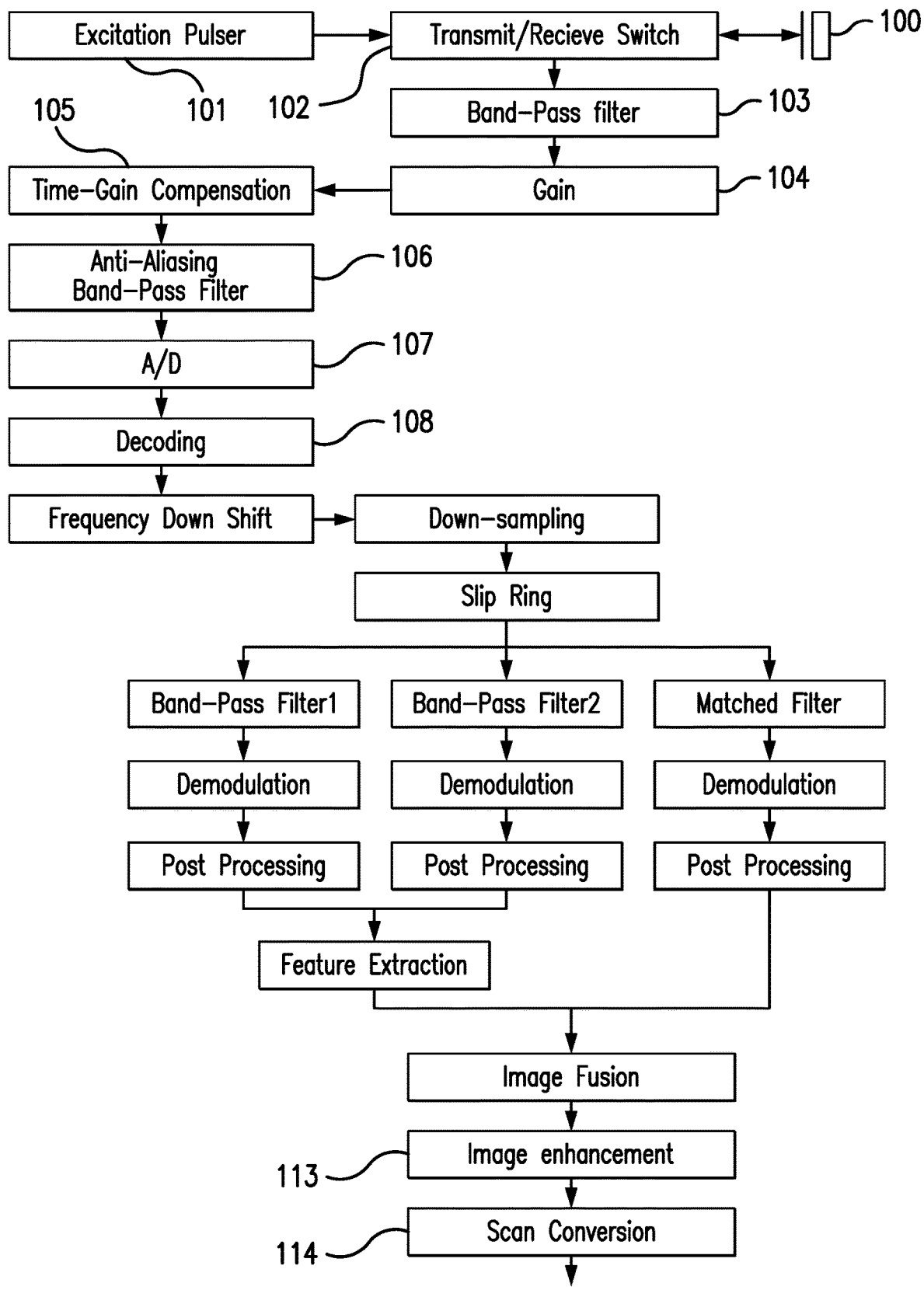
FIG. 1f shows another implementation example aimed at achieving frequency compounding operations of FIG. 1d.

FIG. 1*f* shows another exemplary implementation of frequency compounding methods shown in FIG. 1*d* with the focus on illustrating where different operations take place physically. In this example, all the operations 100-106 before A/D 107 may be performed in analog domain through analog circuits. All operations between A/D 107 and the slip ring may be implemented on either an FPGA or a DSP chip, which may rotate with the catheter. Remaining operations may be implemented using printed circuit boards.

Figure 1G:
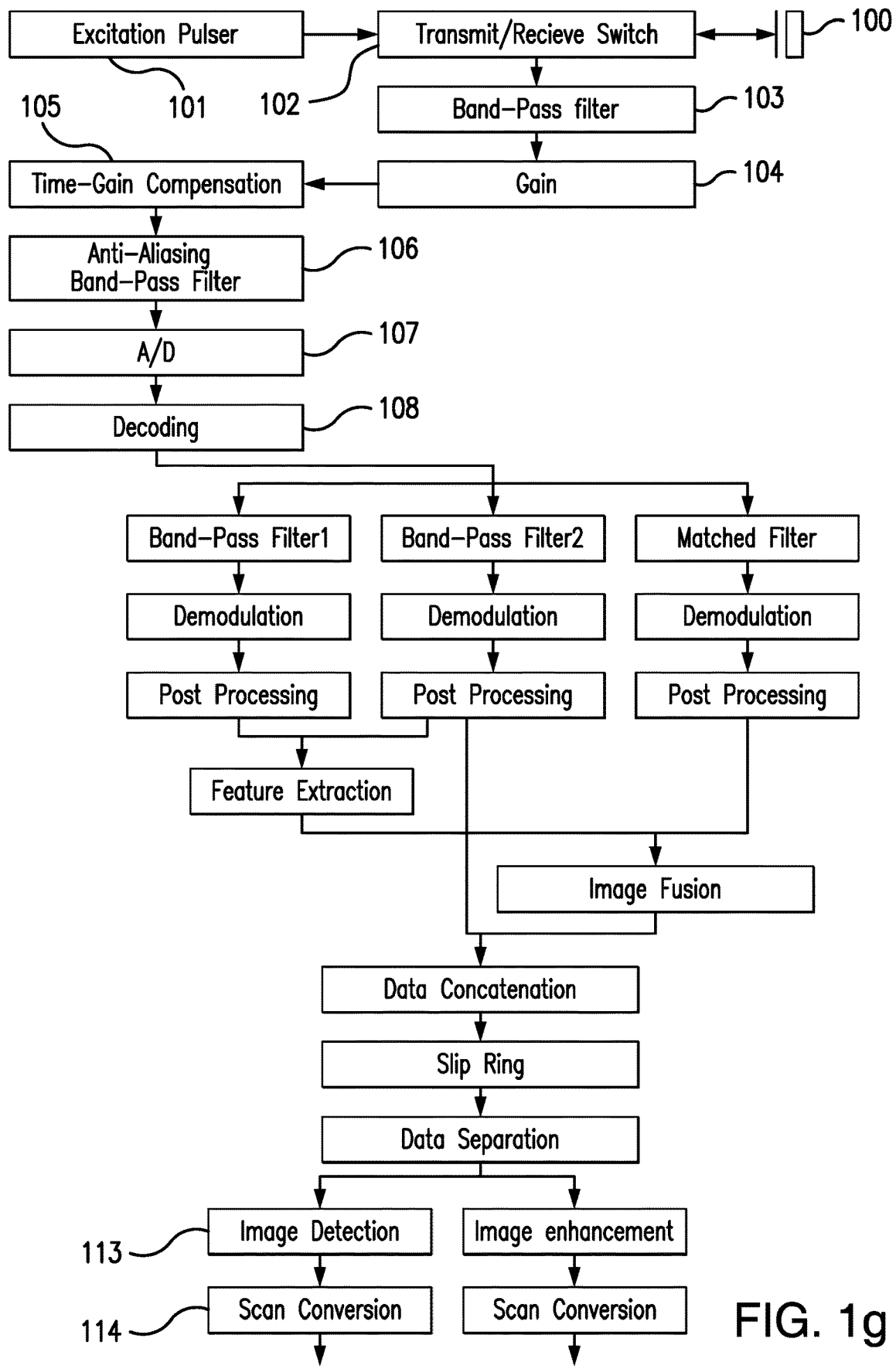
FIG. 1g shows an example of physical arrangement for various operations of the frequency compounding methods of the invention.

FIG. 1*g* shows another example of physical arrangement for various operations of the frequency compounding methods of the invention. This figure shows an extension of FIG. 1*e*: the output of image fusion block and data from band-pass filter 2 channel may be combined together through a data concatenation block, e.g., padding data from band-pass filter 2 channel after data from image fusion block. After the slip ring, the data may be retrieved through data separation block. The data from image fusion block may be used for transverse IVUS image visualization with good spatial and contrast resolution. At the same time, data from band-pass filter 2 channel may be sufficient for tissue characterization, e.g. low-frequency subband image may have sufficient blood speckle suppression, therefore making it easier for lumen detection. Note that because data from band-pass filter 2 channel may be of a relatively smaller bandwidth (for example, filter 2 with a pass-band range of 25 MHz to 45 MHz, bandwidth of 20 MHz, as compared to transducer with pass-band of 25 MHz to 75 MHz, bandwidth of 50 MHz), higher down-sampling rate (such as twice higher) may be used and a smaller amount of data can be transmitted without aliasing.

Figure 1H:
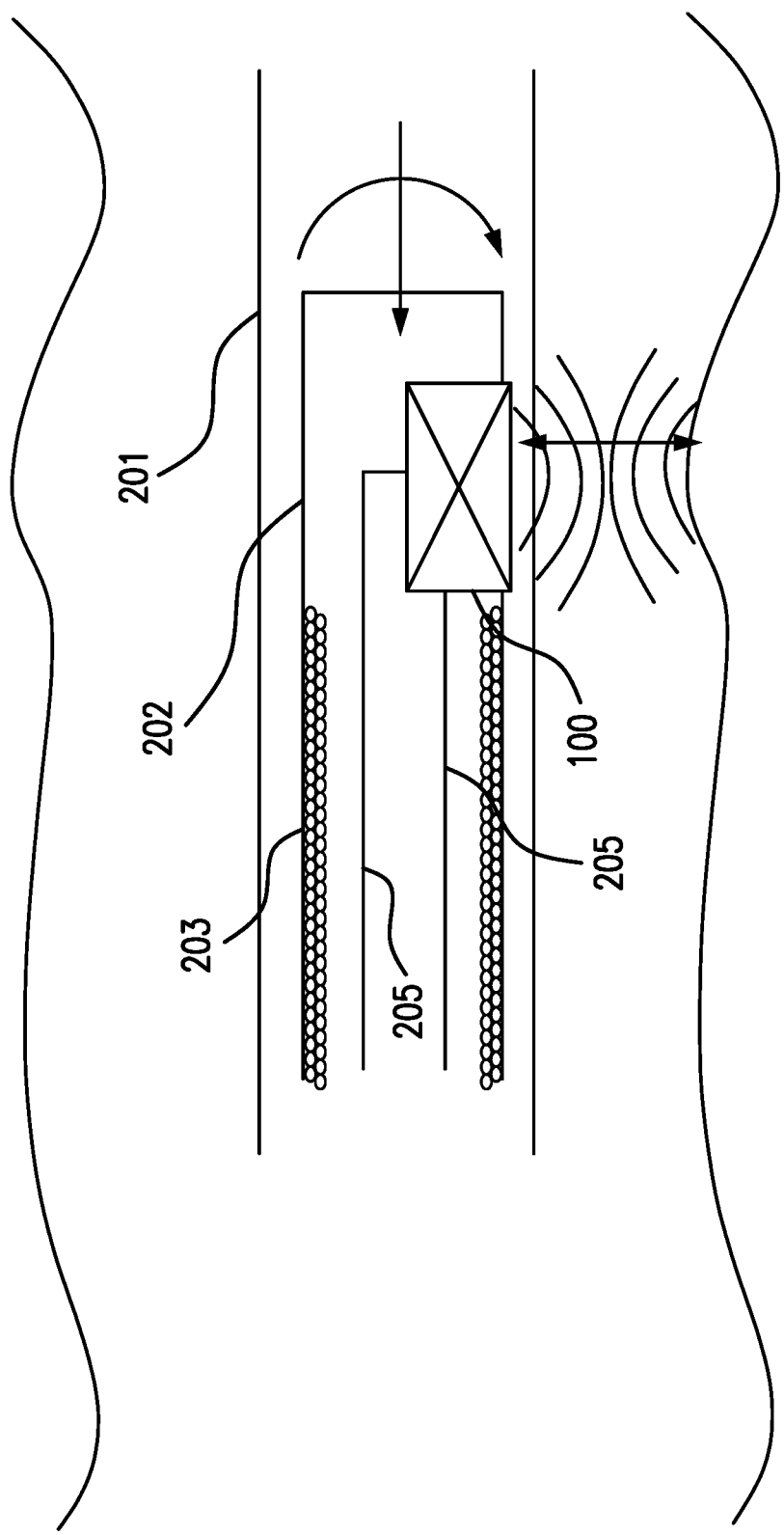
FIG. 1h shows a cross-sectional view of the distal portion of the catheter.

The details of the elongated distal end of the catheter are shown in FIG. 1*h*. The rotatable imaging assembly 202 may be contained within a sheath 201 to separate it from the tissue and circulating blood. The rotatable imaging assembly 202 may include a braided torque cable 203 to facilitate rotation and axial movement of the imaging assembly 202 inside the sheath 201. The imaging assembly further includes an ultrasound transducer 100 energized by one or more electrical conduits 205. The ultrasound transducer 100 may be configured to emit ultrasound energy towards the blood vessel wall and receive reflected energy from the blood vessel wall.

The desired chirp waveform may be achieved through traditional approach with the following constraints: (i) limited duration so that the near field won't be sacrificed by the edge effects, and/or (ii) the waveform may be weighted to compensate for the frequency-dependent tissue attenuation, and/or (iii) the waveform may be apodized (weighted) to suppress range lobes, which may create ringing artifacts in the received echo signal.

Subband decomposition principles are now described in greater detail. The goal of subband decomposition using either filter bank analysis or regular linear filtering is to summarize, categorize, and extract tissue features of interest into different subbands. That allows image enhancement to be performed at a later phase of the analysis by combining those features of interest together. For example, if the user is interested in blood speckle, then a subband with a center frequency F2 in the high frequency range may be used to provide blood speckle of higher intensity; if the user is interested in tissue data in the far field on the other hand, then a subband with a center frequency F1 in the low frequency range may be used to preserve more tissue data in the far field; if the user is interested in the image with high resolution, then the full-bandwidth image may be used to present tissue with high resolution.

Depending on a particular application, certain features may need to be more isolated from other features. In these cases, relatively smaller bandwidths may be selected for each subband, such that they do not overlap with each other. In cases where it is desirable to extract features of higher resolution, relatively large bandwidths may be selected for each subband, such that they may overlap with each other— see FIG. 2*d* and description below. When more than two features are of interest, the entire data may be decomposed into more than two subbands, such as seen in FIGS. 2*c*, 2*e* and 2*f* and described below.

Depending on a particular application, different subbands may be designated with the same or different bandwidths, such subbands may be symmetric or non-symmetric with respect to the center frequency of the ultrasound transducer 100.

When filter-bank based analysis is used for subband decomposition, the corresponding filter-bank based synthesis may be used to gracefully reconstruct the image from individual subbands. Alternatively, the user may choose to reconstruct the image through linear or non-linear combination of subband images.

Figure 2A:
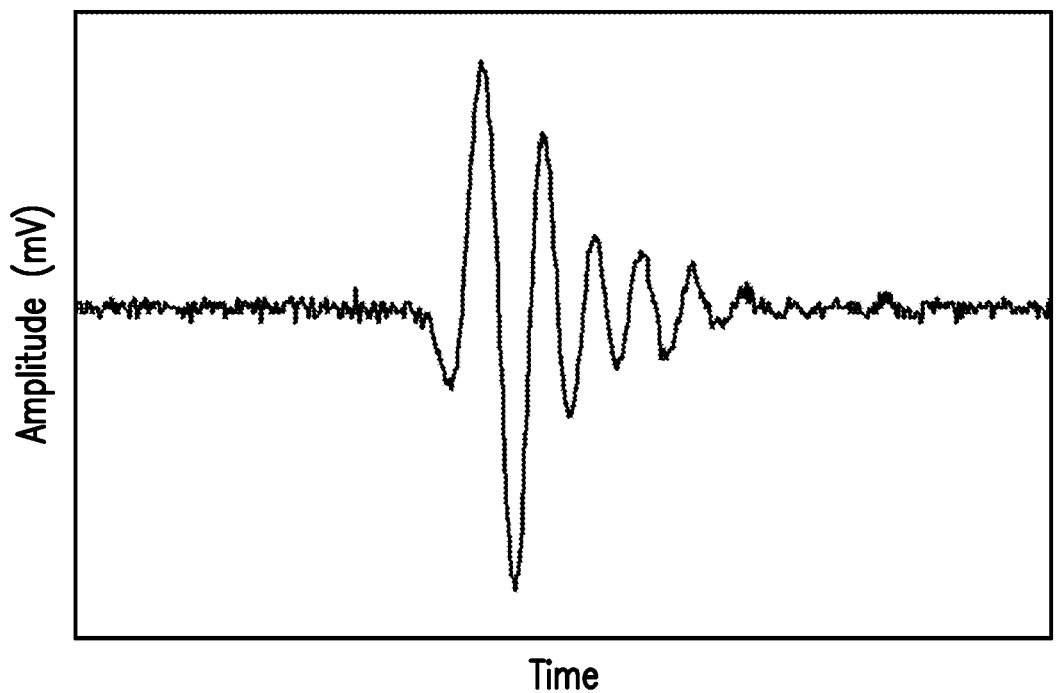
FIG. 2a shows an exemplary IVUS echo response in time domain.
Figure 2B:
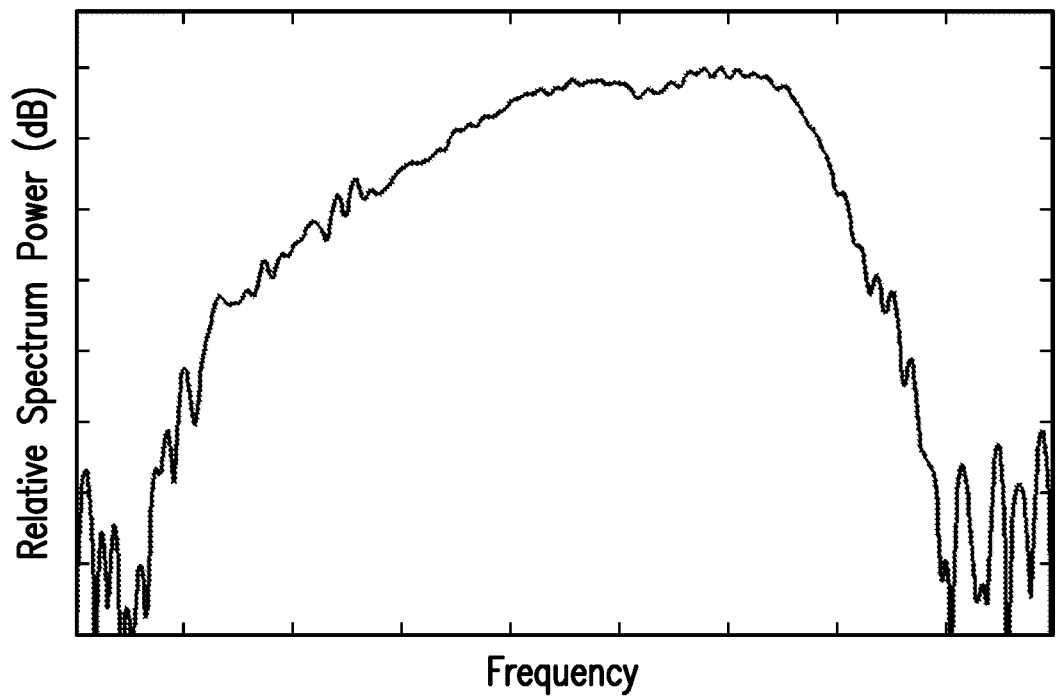
FIG. 2b shows the same IVUS echo response in frequency domain.
Figure 2C:
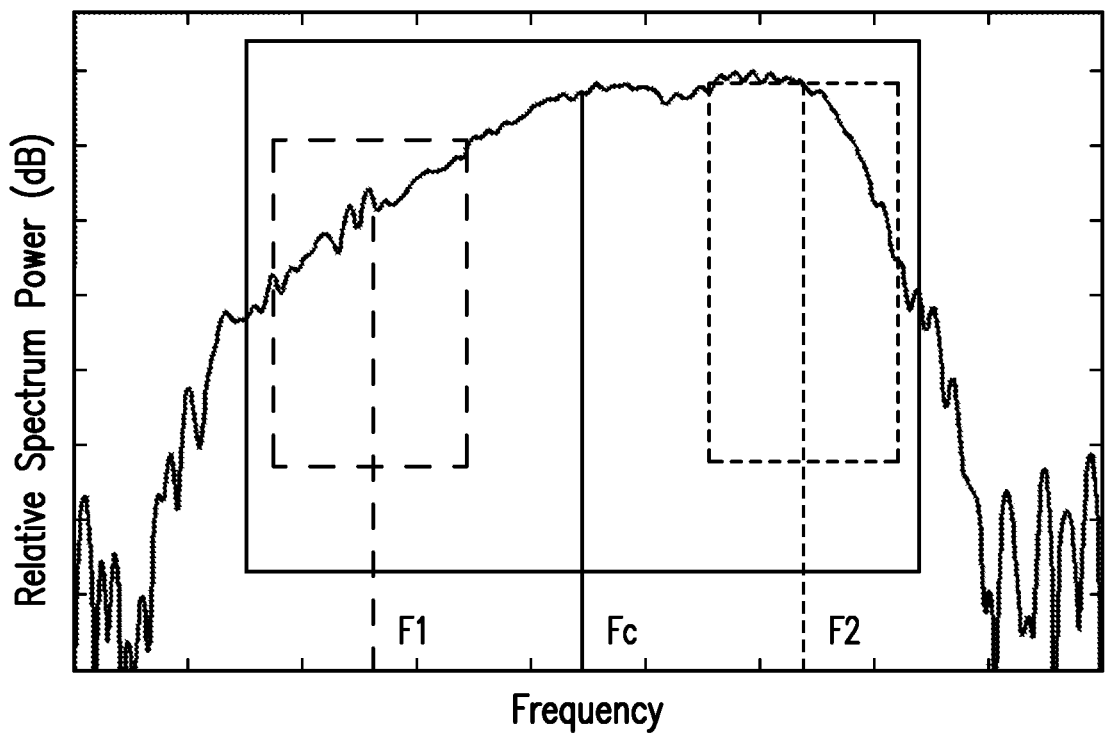
FIG. 2c shows one example of subband division in filter-bank analysis.

FIG. 2*a* shows an example of an IVUS echo response vs. time domain. Its corresponding power spectrum in frequency domain is illustrated in FIG. 2*b*.

FIG. 2*c* shows one example of subband division in filter-bank analysis. Here F1, F2 and Fc correspond to the center frequencies of the respective subbands with low-frequency, high-frequency and full-bandwidth information. Both the low-frequency subband and high-frequency subband are shown to be within the frequency range of the full-bandwidth subband, but without overlapping each other.

Figure 2D:
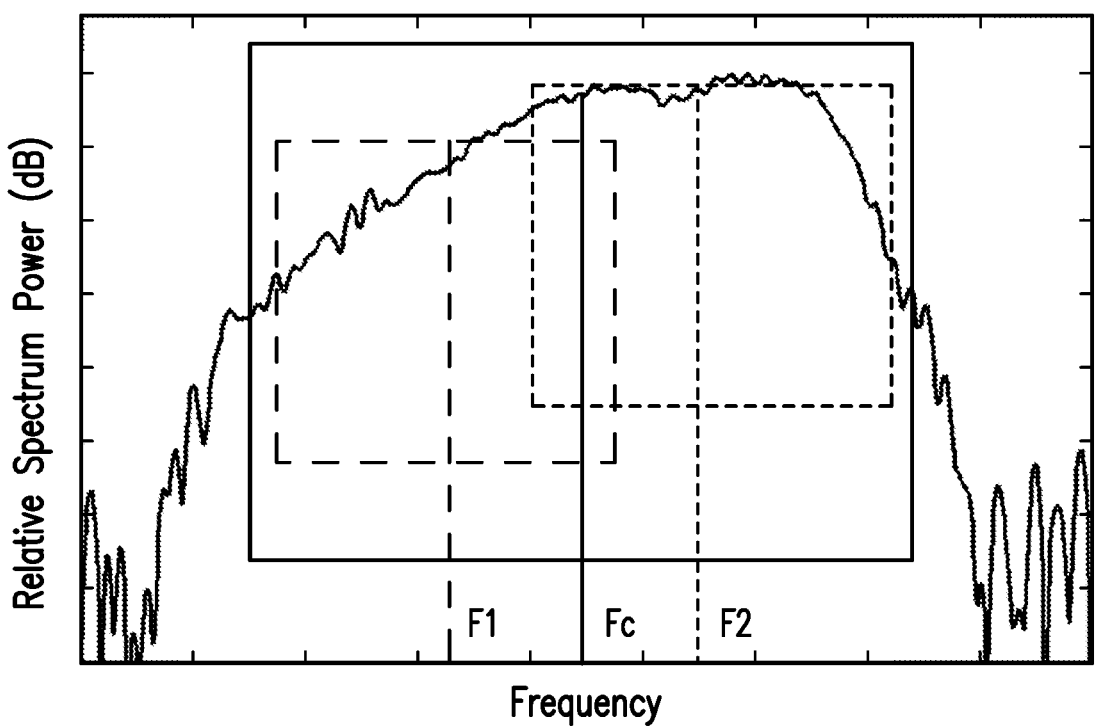
FIG. 2d shows another example of subband division in filter-bank analysis.
Figure 2E:
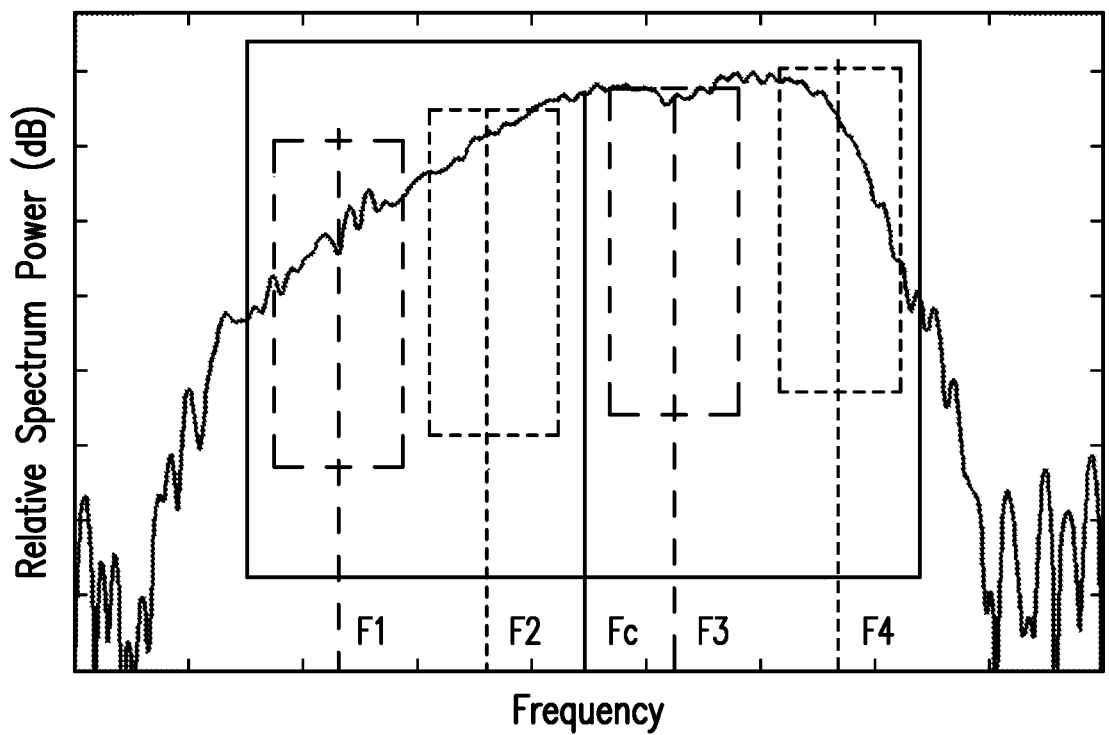
FIG. 2e shows yet another example of subband division in filter-bank analysis.
Figure 2F:
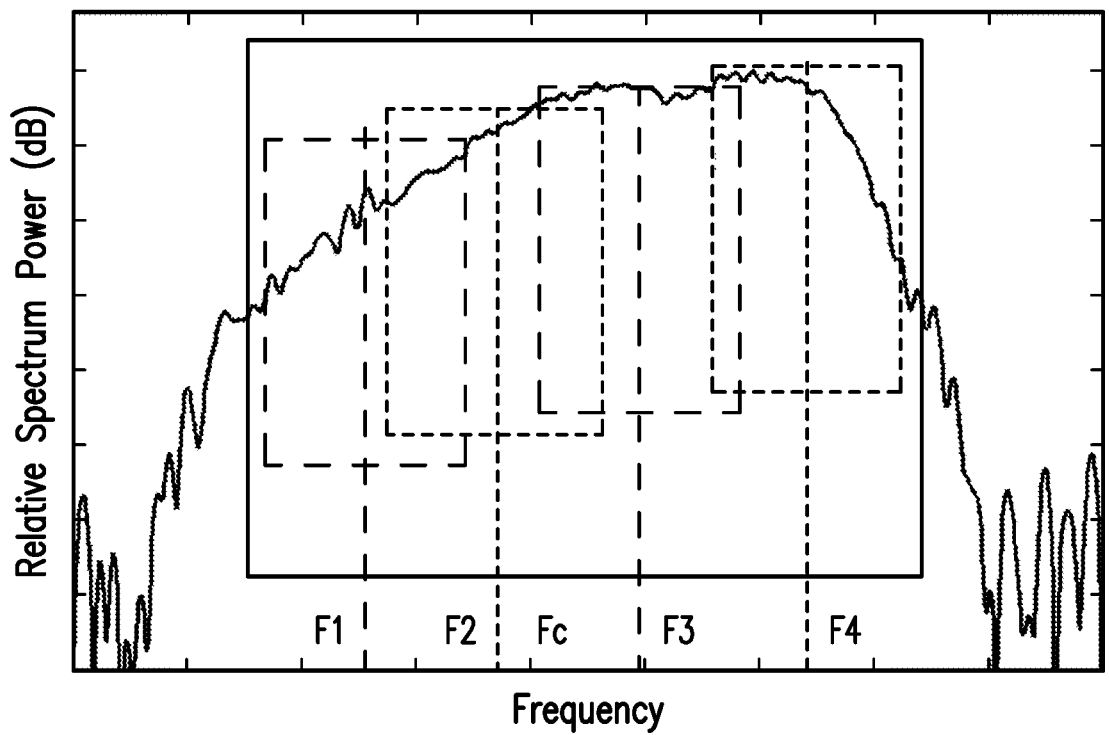
FIG. 2f shows yet a further example of subband division in filter-bank analysis.

FIG. 2*d* shows another example of subband division in filter-bank analysis. As compared to the example shown in FIG. 2*c*, the low-frequency subband and high-frequency subband may be overlapped.

FIG. 2*e* shows yet another example of subband division in filter-bank analysis. As compared to FIG. 2*c*, in addition to full-bandwidth subband with center frequency Fc, subbands with center frequencies of F1, F2, F3, F4 are adopted, so that more refined information from different frequency ranges may be extracted. Other implementations may include subbands with center frequency other than 2 or 4.

FIG. 2*f* shows yet a further example of subband division in filter-bank analysis. As compared to FIG. 2*e*, the subbands with center frequencies of F1, F2, F3 and F4 may be overlapped.

Figure 3A:
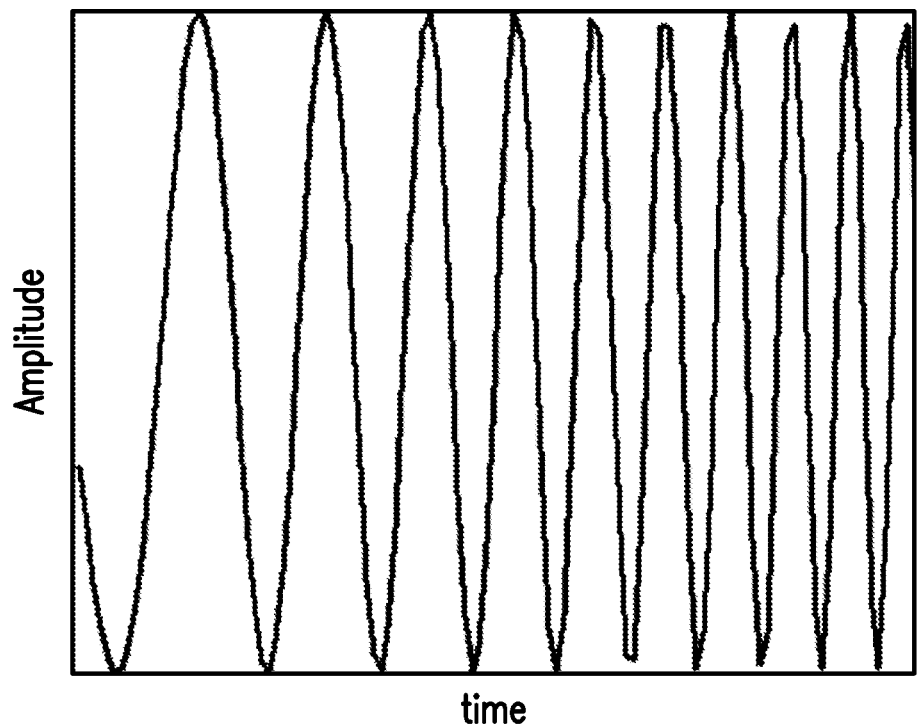
FIG. 3a shows an example of a chirp pulse in time domain.

FIG. 3*a* shows an example of chirp pulse in time domain, which varies from starting low frequency F_L0 to ending high frequency F_H0.

Figure 3B:
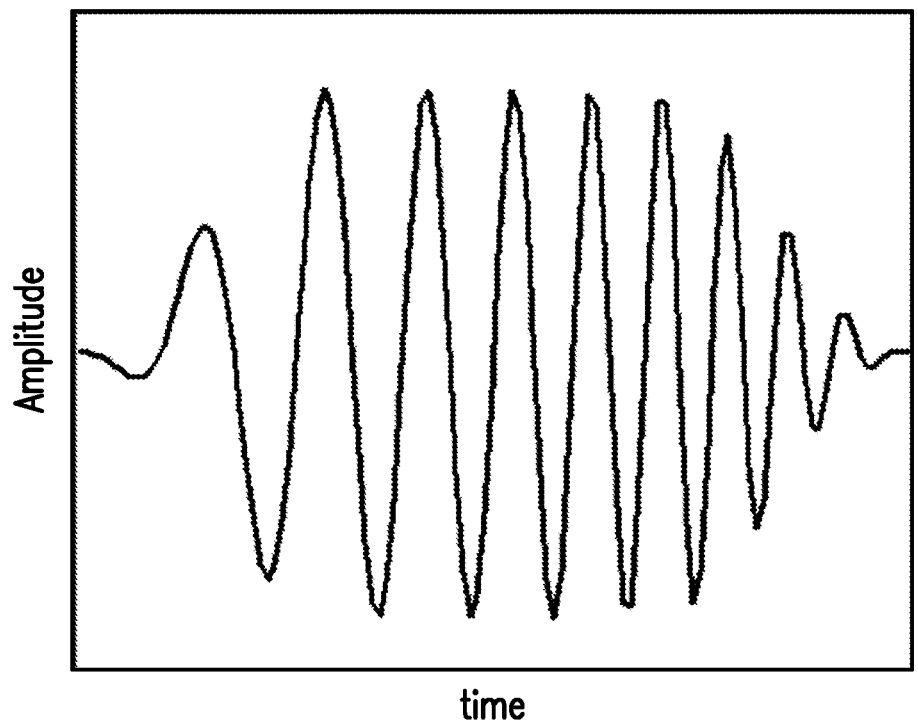
FIG. 3b shows an example of the chirp pulse in FIG. 3a, which is weighted by selected windowing function.

FIG. 3*b* shows an example of chirp pulse in FIG. 3*a*, which is weighted by selected windowing function (it may be created, for example, by multiplying the chirp pulse in FIG. 3*a* by a Gaussian function). The windowing function may be used to suppress potential range lobes of the image (side lobes of the pulse), which may improve the spatial resolution. For example, a multiplicative window using 50% Tukey function may be selected. By selection of proper window, the decoded chirp signal will have fewer side lobes, that is smaller and fewer ringing signal artifacts near the genuine signal.

Figure 3C:
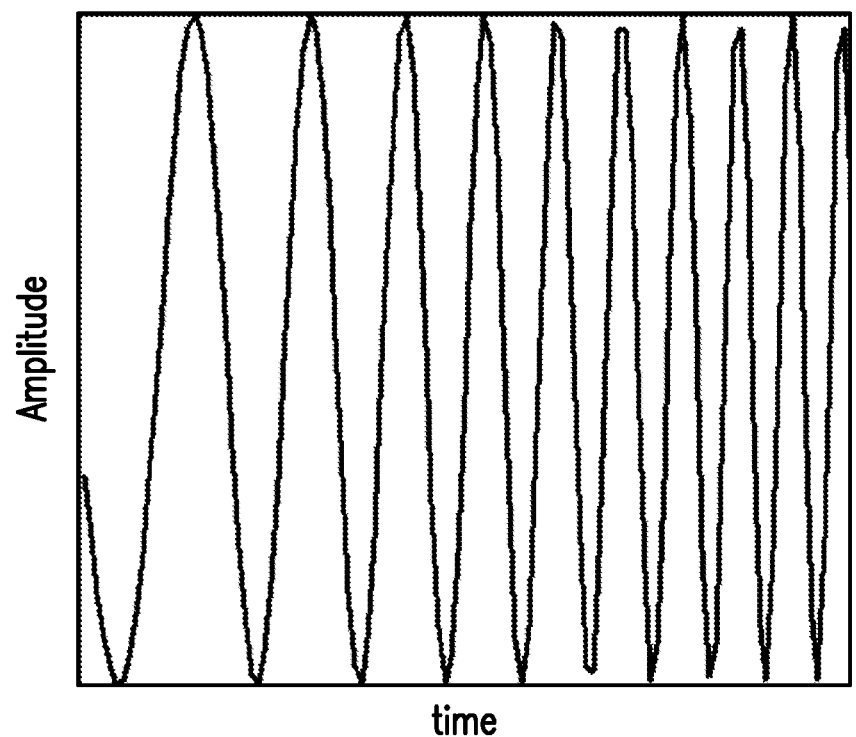
FIG. 3c has another example of a chirp pulse.
Figure 3D:
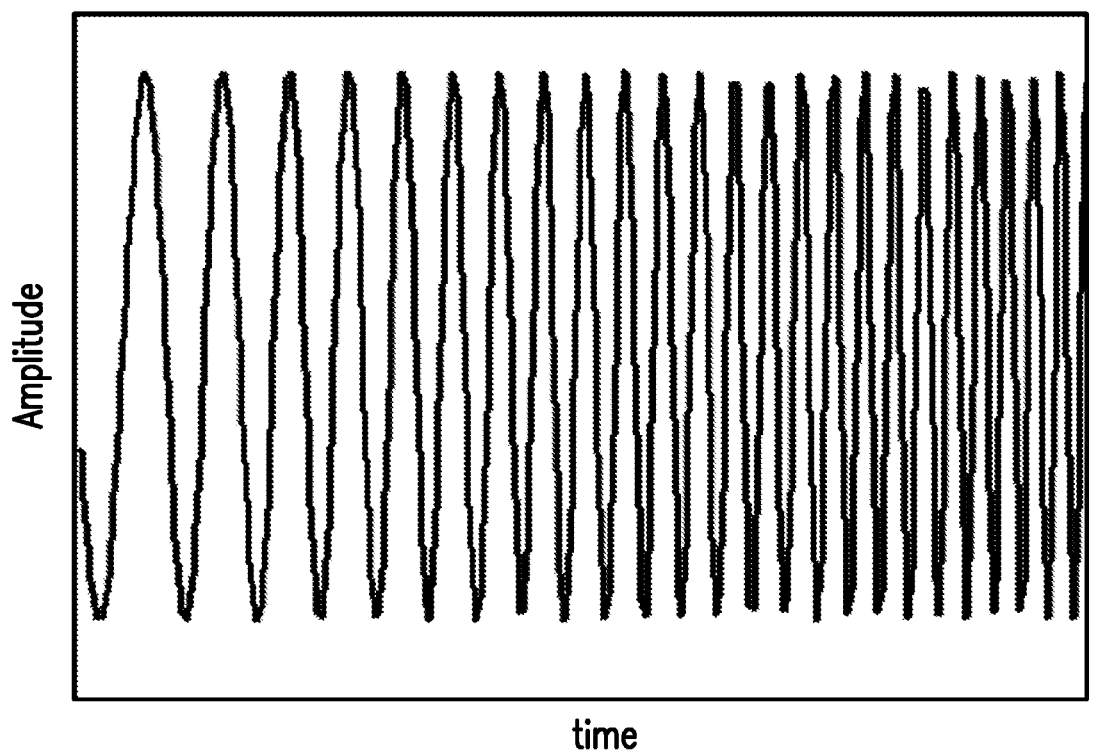
FIG. 3d illustrates yet another example of a chirp pulse.

FIGS. 3c and 3d shows two examples of chirp pulses, with same starting and ending frequencies, but different time durations. FIG. 3d shows longer pulse duration, the corresponding decoded signal may have better depth penetration due to higher Signal-to-Noise ratio. For an imaging application requiring large field of view, the pulse with longer duration may be used. In one example, a Signal-to-Noise ratio may get up to 6 dB higher with the chirp pulse in FIG. 3d having a 400 ns duration as compared to the chirp pulse in FIG. 3c having a 200 ns duration.

Figure 3E:
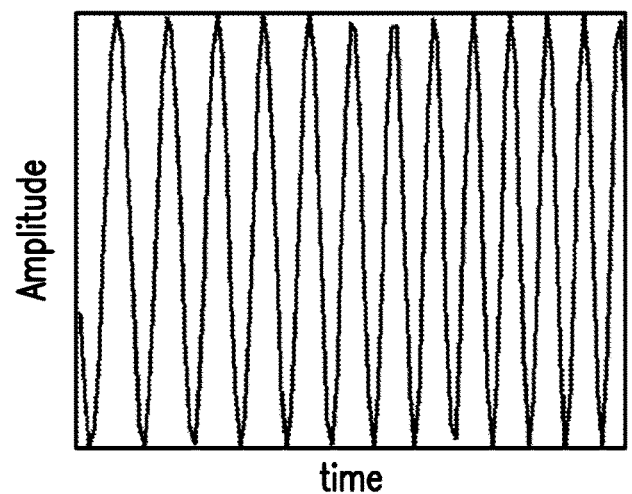
FIGS. 3e through 3g show three examples of chirp pulses, with same duration of time but at different frequency ranges.
Figure 3F:
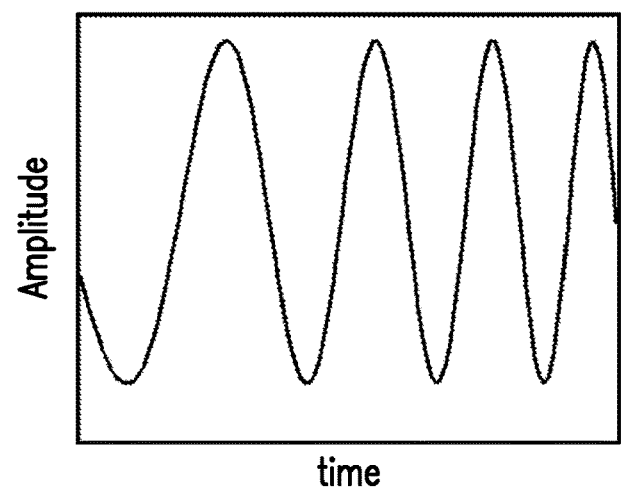
Figure 3G:
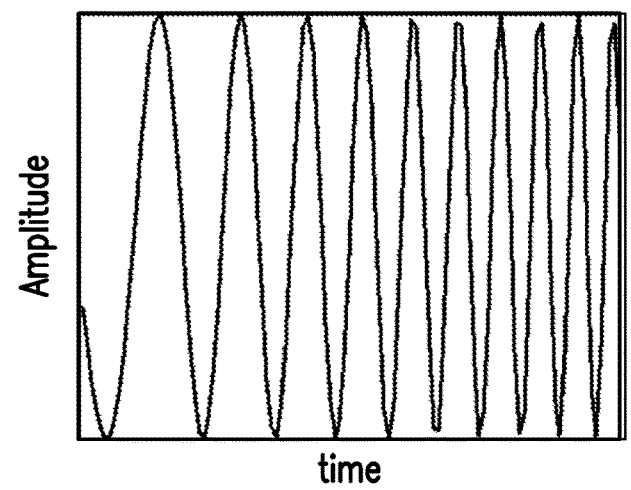

FIGS. 3e to 3g show three examples of chirp pulses, with same duration of time but at different frequency ranges. The chirp pulse in FIG. 3e has a wide frequency range [F_L1, F_H1, for example 20 and 80 MHz respectively and 200 ns duration], which may capture tissue information from a wide range with good spatial resolution. The chirp pulse in FIG. 3f has a relatively narrower frequency range [F_L2,F_H2, for example 20 and 30 MHz respectively and 200 ns duration], with F_L2=F_L1 and F_H2<F_H1, but relatively more energy in the corresponding lower frequency range. This will preserve more tissue data of low frequency response. The chirp pulse in FIG. 3g has a relatively narrower frequency range [F_L3,F_H3], with F_H3=F_H1 and F_L3>F_L1, but relatively more energy in the corresponding higher frequency range. This will preserve more tissue data of a high frequency response.

Figure 3H:
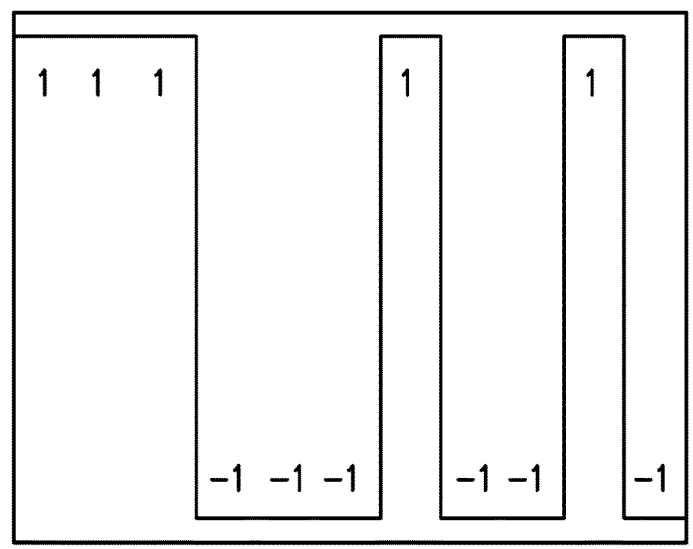
FIGS. 3h through 3j show examples of coded pulses using binary encoding.
Figure 3I:
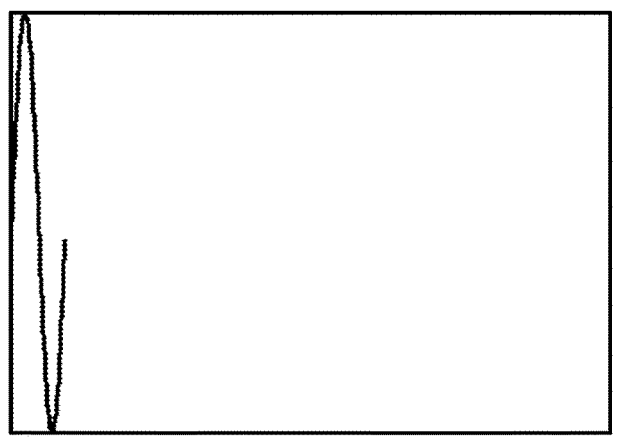
Figure 3J:
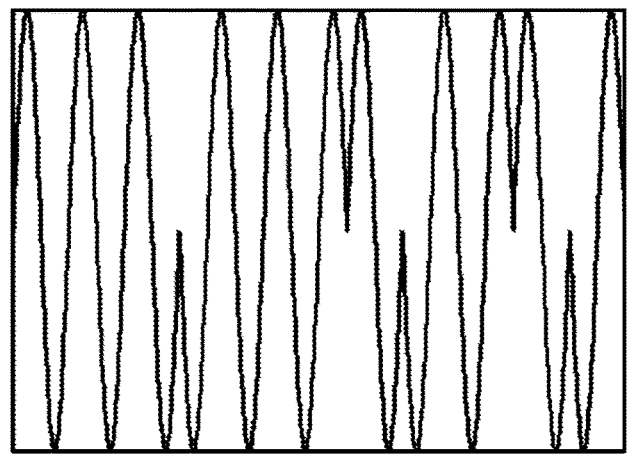

The chirp pulser may be operated to sweep from a starting frequency through an ending frequency continuously. Other forms of multi-frequency waveform signals may also be used for the purposes of the present invention, such as for example a Barker code and a Golay code. These are exemplary binary codes with two discrete values: 0 or –1 and 1. Similar to a chirp signal, these codes may transfer more energy to the ultrasound transducer by using a longer pulser while still maintaining good spatial resolution through pulse compression. An example of encoding using a Barker code is shown in FIGS. 3h through 3j. FIG. 3h shows an exemplary Barker code, FIG. 3i is the bipolar pulse used in a traditional system, FIG. 3j is the Barker encoded pulser by modulating FIG. 3i with FIG. 3h. The resulted Barker-encoded pulser will have a multi-frequency range with good pulse compression property as switching from one segment of the waveform to another inevitably causes transitional frequency changes in the ultrasound transducer.

Given the above description, the term "multi-frequency waveform" is used herein to describe both the chirp encoding methods as well as the binary encoding methods including a Barker code and a Golay code.

Figure 4A:
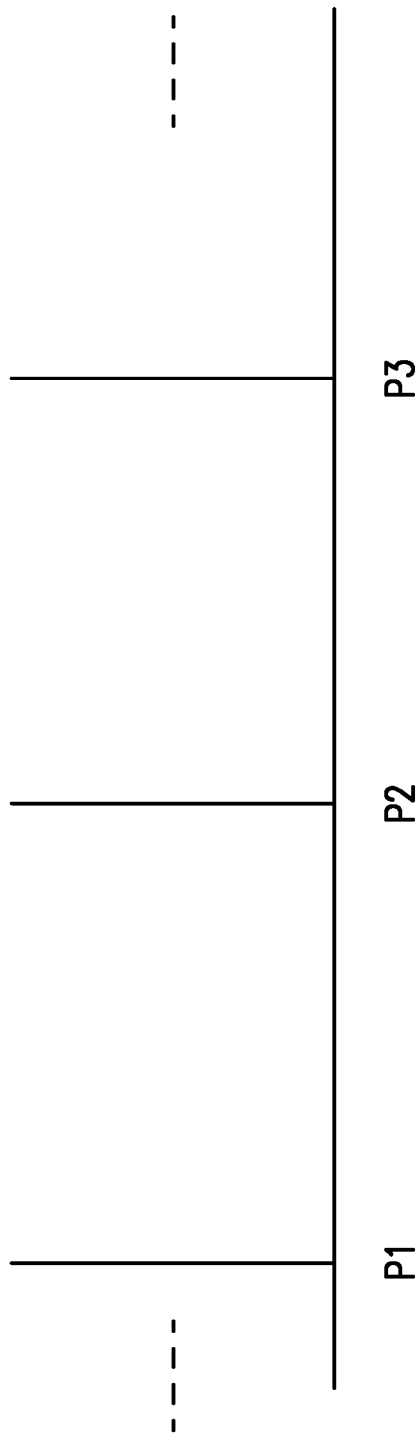
FIG. 4a is an illustration of a uniform pulser signal distribution.
Figure 4B:
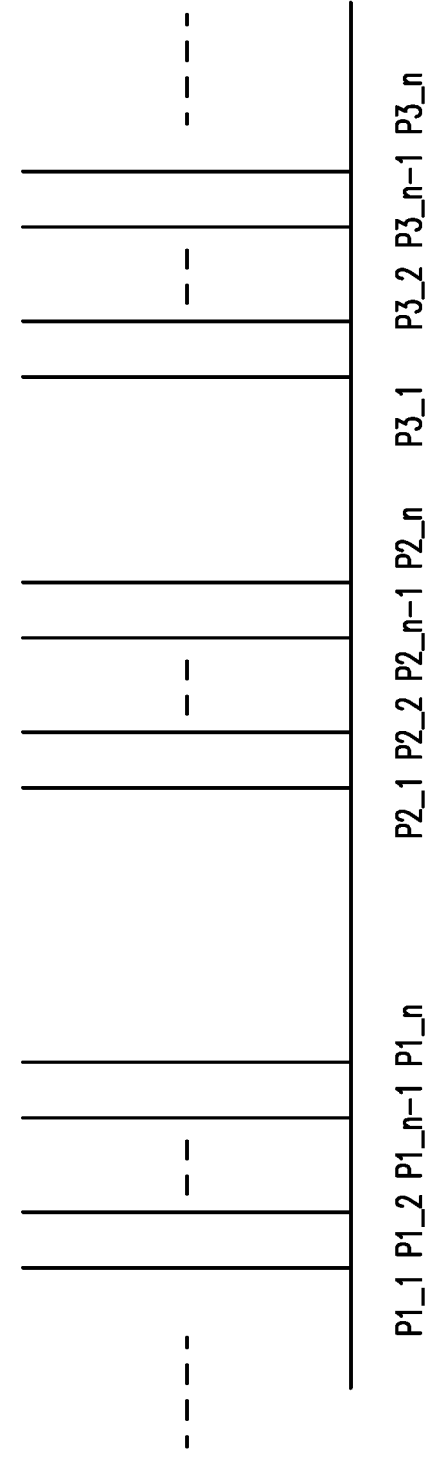
FIG. 4b is an illustration of a non-uniform pulser signal distribution.

FIG. 4a is an illustration of a uniform pulser signal distribution, where same pulser signal P1, P2, P3 etc. may be used to excite the piezoelectric transducer 100 and receive the echo signal so as to form each a-line. In comparison, FIG. 4b gives an illustration of a non-uniform pulser signal distribution, where still the same pulsers may be used, wherein the received echo signals received from the piezoelectric transducer 100 excited by Pm_1 to Pm_n (m=1, 2, 3 etc) may be combined together (linearly or non-linearly) to generate a single a-line. The linear combination may be performed for example as a standard boxcar averaging operation, while the non-linear combination may be performed for example as a median filtering. The resulted a-line may have relatively higher Signal-to-Noise ratio at the expense of some degree of motion artifacts. For example, with n=4 and a linear box car averaging used, an improvement of up to 6 dB in the Signal-to-Noise ratio may be obtained.

In embodiments, the inter-a-line filtering (a-line averaging) may be performed before or after the operations of the decoding block. In this case, boxcar averaging of the neighboring a-lines may be also deployed, as well as other linear or non-linear filtering operations for the purposes of increasing Signal-to Noise ratio.

Figure 5A:
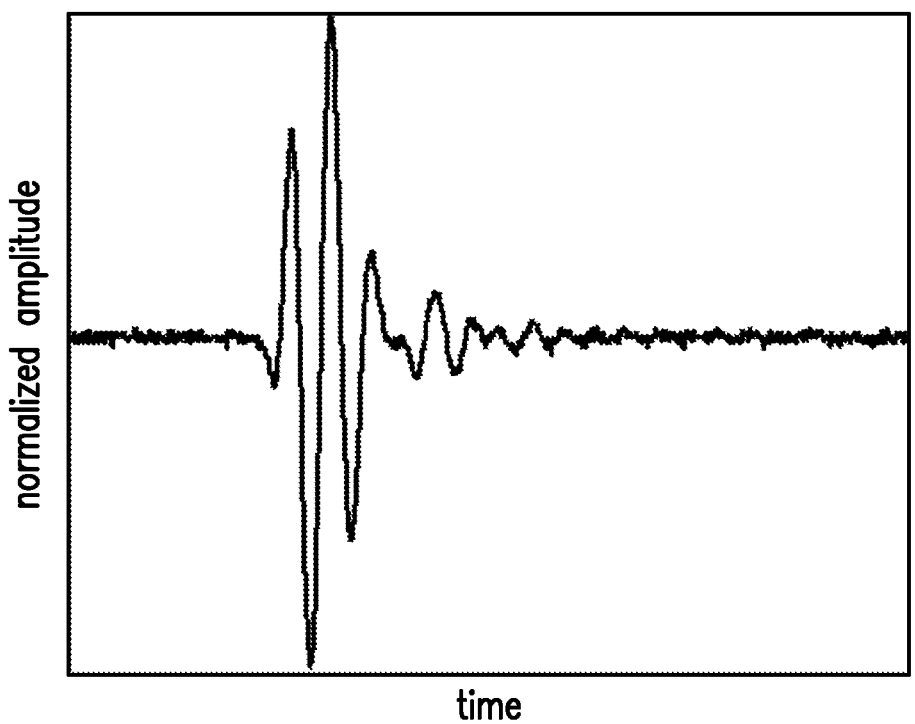
FIGS. 5a through 5d show an example of an encoding and decoding process.
Figure 5B:
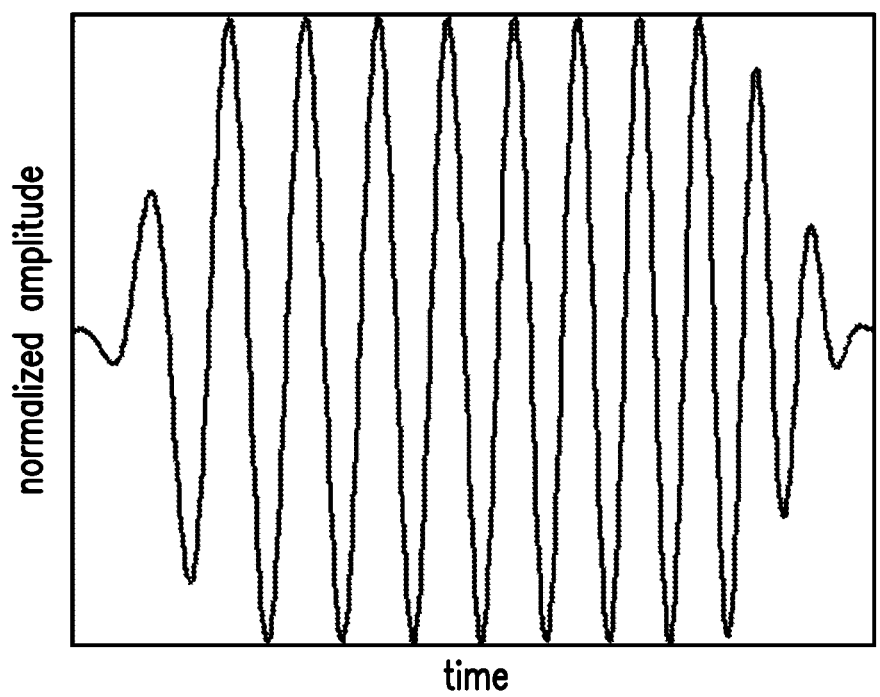
Figure 5C:
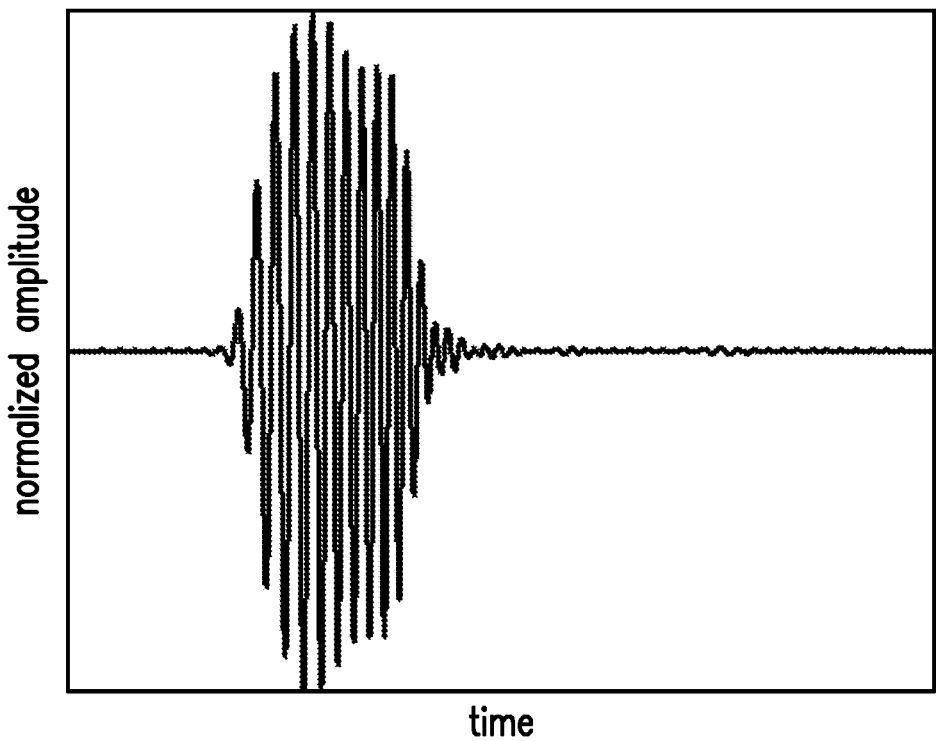
Figure 5D:
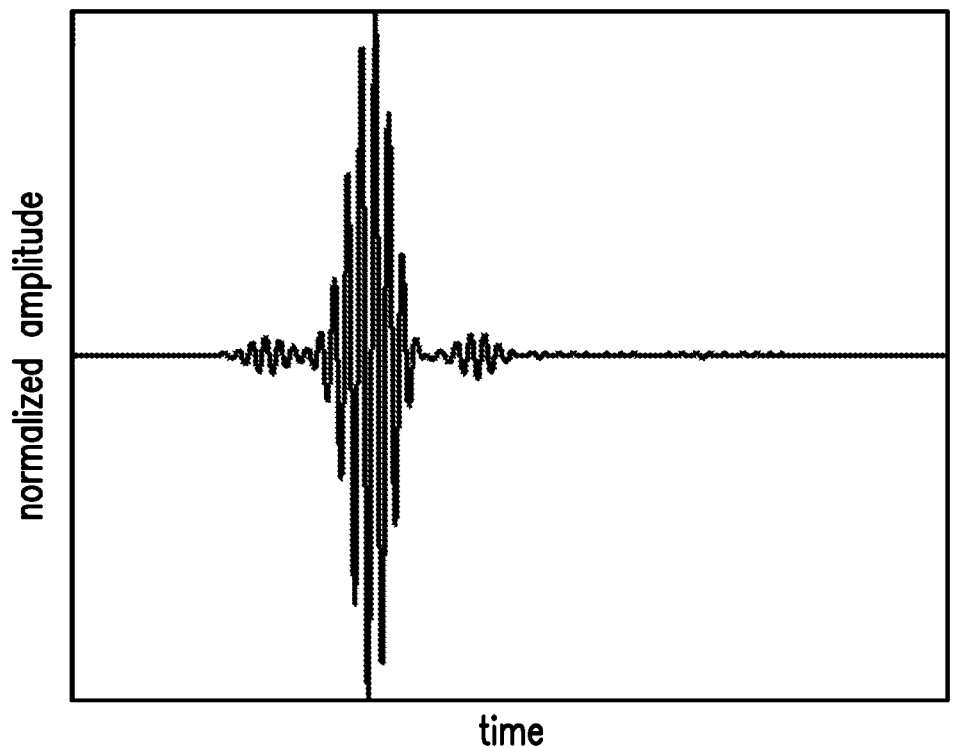

Various coded pulsers may be used for this purpose as described in more detail below. Examples of such coded pulsers include Chirp encoding, Baker encoding, Golay encoding, and others known in the art. When the signal is received directly from a system using coded excitation and the pulser is carefully configured to perform pulse compression, that signal may be viewed as the ultrasound transducer's impulse response signal, which is encoded by the pulse. It may therefore require proper decoding to retrieve the signal with high signal-to-noise ratio (due to the signal boost while the noise level stays the same) and small range lobes (to maintain similar resolution). One decoding method which can be used for this purpose may be matched filtering using the excitation pulser. In some cases, carefully selected weighting functions may also be used in match filtering to suppress the range lobes. FIGS. 5a through 5d show an example of an encoding and decoding process. FIG. 5a shows an echo signal collected using a traditional unipolar pulse, this signal may serve as a reference. FIG. 5b shows a weighted chirp excitation pulse, FIG. 5c shows the corresponding received echo signal. Due to a long excitation pulse, the directly received echo signal has longer duration, which will lead to lower resolution. FIG. 5d shows the echo signal after performing matched filtering of raw echo in FIG. 5c with a pulser in FIG. 5b. Note that the decoded echo has a relatively low noise floor, and thus higher Signal-to-Noise ratio while the echo duration is short.

The signal processing methods described above may allow higher contrast resolution (through chirp and frequency compounding) resulting in better boundary identification, such as lumen boundary discrimination. The methods of the invention may also allow reaching higher spatial resolution (through the use of wide bandwidth transducer) resulting in better feature identification, e.g. intimal plaque cap thickness.

Coded Pulser Description

The following describes the principles of operation and hardware of the novel coded pulser of the present invention. Multi-frequency or broadband pulse waveform is needed to energize the piezoelectric transducer 100 to emit an ultrasonic signal. That multi-frequency waveform may be produced by the coded pulser. A waveform may be generated by the pulser by sweeping through a predetermined frequency range. To improve Signal-to-Noise ratio while maintaining good spatial resolution, various pulsing compression techniques (code modulated excitation, such as Chirp, Golay, Barker, etc.) may be adopted.

A digital to Analog converter (DAC) may be used to pulse an ultrasound transducer 100 as described above with a chirp waveform that is digitally generated. In addition, an amplifier capable of driving a low impedance transducer with voltages nearing +/−40V may be used. Repeatable and low-distortion waveforms may allow the chirp de-correlator to accurately detect the received coded data. In some embodiments, the Coded Pulser for high resolution IVUS may include one or more of the following characteristics:

Waveform frequencies from below 10 MHz to above 70 MHz

+/−40 V peak waveforms into approximately 50 ohm transducers

Waveform jitter with respect to IVUS acquisition of under 100 pS

Low harmonic distortion to keep harmonics below EMI limits

Low duty cycle: <1: 300 Output waveform is active for ~200 nS at a repetition rate of 4 pulses×4 KHz (16 KHz=62.5 µs).

In some embodiments, the pulser may have low power consumption, low component cost and/or low printed circuit board cost.

The DAC sample rate may be a function of the required highest IVUS frequency, which, in a non-limiting embodiment, may be above 70 Mhz. In one embodiment, the IVUS ADC may operate at 300 MHz. Low jitter (e.g., under 100 pS) may result when the pulser DAC and the ADC operate at either the same clock or at integer sub-multiples of the same clock. On the high end, pulse distortion may limit the sample rate (e.g., to about 300 Mhz). In some embodiments, 300 MHz may be chosen as the Pulser sample rate. 300 MS divided by 70 MHz is 4.3 samples per cycle at 70 MHz, which may provide for a reasonable amount of over-sampling.

In embodiments, the ability to compensate for a limited oversample frequency may be improved with a certain waveform distortion, for example zero-order hold sin c rolloff.

The circuit may take advantage of the low duty cycle characteristic. Components that are rated to handle the high peak currents and voltages may be physically large and thus have high capacitive and inductive parasitics. But because of the low duty cycles, which may be adopted for the purposes of the present invention, power dissipation and temperature rise may be minimized, which may allow physically smaller and faster components with low parasitics to be used instead.

In some embodiments, a 4-bit design approach may be used, while in other embodiments other bit design approach may be used.

Figure 6:
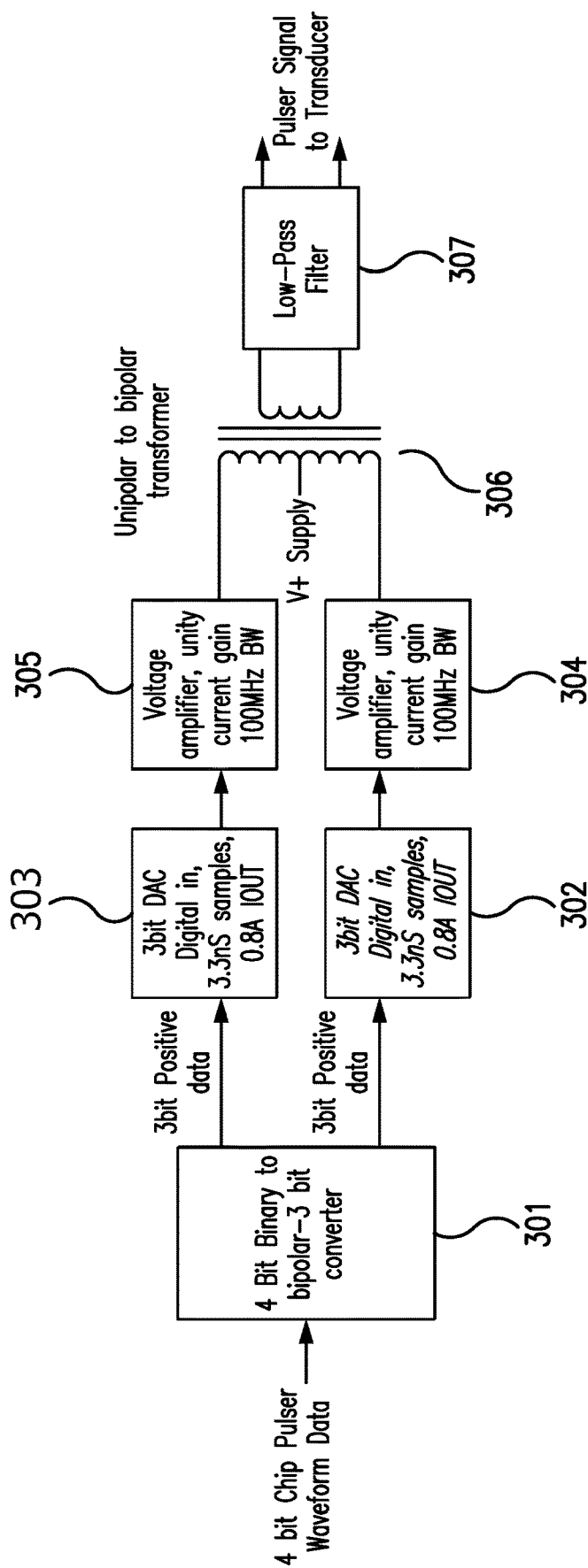
FIG. 6 shows a 4-bit exemplary circuit topology.

A 4-bit exemplary circuit topology is now described with reference to FIG. 6. The current implementation of the circuit topology used is a high current and high voltage, direct DAC. A 4-bit waveform DAC may be comprised via a 4-Bit Binary to bipolar—3 bit converter 301 of two unipolar 3-bit binary scaled DACs 302 and 303 amplified by Voltage gain stages 304 and 305, and combined via a transformer 306 to provide a 4-bit bipolar output signal with respect to signal ground. Output levels may be +/−7, with 0 mid-scale. A $16^{th}$ code would be asymmetric, and so may not be used. At a code of 0, no currents flow in the DACs, thus minimizing power consumption. This is the idle condition. Power is consumed only when the DAC input is non-zero. To achieve this with a separate low power DAC and amplifier, the amplifier must be operated as Class B with no quiescent current, but which may cause crossover distortion. The quiescent current may be increased so that the amplifier is operated as Class AB, but this would use high quiescent power. Because the transformer cannot pass direct current, the waveform must be symmetrical around 0. Unipolar waveforms therefore cannot be used.

In other embodiments, other than 0 code may be used as a mid-scale, with corresponding increase in power consumption while in idle condition.

The DAC transistors in elements 302 and 303 need to switch very fast, with a nominal 1 nanosecond rise and fall times. Transistor current gain (beta), the feedback capacitance (CCB) and the output impedance (drive current) of the logic signals are the limiting factors defining selection of proper components.

A Low Voltage Differential Signaling (LVDS) receiver with 3.3V high output drive current may be selected to drive the DAC. RF transistors rated at 5 V, 500 mA, and with Ft>10 GHz may be chosen for this stage. The bits of the DAC may be binary weighted, each bit providing double the current of the next least significant bit.

This circuit configuration of elements 304 and 305 is generally known as a 'cascode' amplifier. In this configuration, the DAC output current may be coupled to a voltage amplifier the emitter of a common-base output transistor 305 and 306. A cascode stage may be used here to minimize the 'Miller effect'. Miller effect refers to the output of an amplifier, which is capacitively coupled to the input, causing negative feedback at high frequencies and thus reduced high frequency response. The output transistors may be selected to handle high voltage up to 100V or more but do not need to be as fast as the input transistors. Transistors in the 200 MHz Ft range may be used.

Current Vs. Voltage Drive

The output filter 307 may pass the chirp pulser signals and may reduce their $2^{nd}$, $3^{rd}$ and higher harmonics. The filter may be driven by a current source and may be loaded by the coax and transducer.

The digitally generated waveforms may be modified to improve the output waveform. For example, they can apply pre-emphasis (by reducing low frequencies and increasing high frequencies) to compensate for circuit and sin x/x high frequency rolloff, or can use sigma-delta modulation techniques to optimize the frequency response of the waveform.

What is claimed is:

1. A pulser for ultrasound imaging, the pulser comprising:
   a binary to bipolar converter;
   a first 3-bit digital to analog converter (DAC) configured to convert only a first 3-bit digital output of the binary to bipolar converter to a first analog output;
   a second 3-bit DAC configured to convert only a second 3-bit digital output of the binary to bipolar converter to a second analog output;
   a first voltage amplifier configured to amplify only the first analog output;
   a second voltage amplifier configured to amplify only the second analog output; and
   a transformer configured to combine only the amplified first analog output and the amplified second analog output and output a multi-frequency or broadband pulser signal.

2. The pulser of claim 1, further comprising a low-pass filter configured to pass the pulser signal and reduce second and third harmonics.

3. The pulser of claim 1, wherein the first and second DACs are unipolar DACs.

4. The pulser of claim 1, wherein the first DAC consumes power only when an input to the first DAC is non-zero, and the second DAC consumes power only when an input to the second DAC is non-zero,
   wherein the input to the first DAC is the first 3-bit digital output of the binary to bipolar converter, and the input to the second DAC is the second 3-bit digital output of the binary to bipolar converter.

5. The pulser of claim 1, wherein the first and second voltage amplifiers are operated as Class B with no quiescent current.

6. The pulser of claim 1, wherein the first and second voltage amplifiers are operated as Class AB.

7. The pulser of claim 1, wherein the first and second voltage amplifiers each have a cascode configuration.

8. An intravascular ultrasound imaging system comprising:
a pulser including:
a binary to bipolar converter,
a first 3-bit digital to analog converter (DAC) configured to convert only a first 3-bit digital output of the binary to bipolar converter to a first analog output,
a second 3-bit DAC configured to convert only a second 3-bit digital output of the binary to bipolar converter to a second analog output,
a first voltage amplifier configured to amplify only the first analog output,
a second voltage amplifier configured to amplify only the second analog output, and
a transformer configured to combine only the amplified first analog output and the amplified second analog output and output a multi-frequency or broadband pulser signal; and
an imaging assembly comprising an ultrasonic transducer configured to be energized by the multi-frequency or broadband pulser signal to emit ultrasound energy towards a target blood vessel,
wherein the imaging assembly is configured to receive ultrasound energy reflected by the target blood vessel.

9. The intravascular ultrasound imaging system of claim 8, further comprising a receiver configured to decompose said reflected ultrasound energy into a plurality of individual subband signals, individually process said plurality of subband signals, and then reconstitute said plurality of subband signals into one or more imaging signals representing the target blood vessel.

10. The intravascular ultrasound imaging system of claim 8, wherein the pulser further includes a low-pass filter configured to pass the pulser signal and reduce second and third harmonics.

11. The intravascular ultrasound imaging system of claim 9, wherein the receiver is configured to reconstitute said plurality of subband signals into one or more imaging signals representing the target blood vessel by non-linearly combining said individually processed plurality of subband signals.

12. The intravascular ultrasound imaging system of claim 9, wherein the receiver is configured to reconstitute said plurality of subband signals into one or more imaging signals representing the target blood vessel by linearly combining said individually processed plurality of subband signals.

13. The intravascular ultrasound imaging system of claim 9, wherein the plurality of individual subband signals includes a first subband signal and at a second subband signal, wherein the first subband signal is a full bandwidth signal, and the second subband signal has a center frequency that is lower or higher than a center frequency of the full bandwidth first subband signal.

* * * * *